(12) United States Patent
Bjornvad et al.

(10) Patent No.: US 9,273,104 B2
(45) Date of Patent: Mar. 1, 2016

(54) METHODS FOR PRODUCING SECRETED POLYPEPTIDES HAVING BIOLOGICAL ACTIVITY

(71) Applicants: Novozymes A/S, Bagsvaerd (DK); Novozymes, Inc., Davis, CA (US)

(72) Inventors: Mads Bjornvad, Virum (DK); Debbie Yaver, Davis, CA (US)

(73) Assignees: NOVOZYMES, INC., Davis, CA (US); NOVOZYMES A/S, Bagsvaerd (DK)

( * ) Notice: Subject to any disclaimer, the term of this patent is extended or adjusted under 35 U.S.C. 154(b) by 168 days.

(21) Appl. No.: 14/081,340

(22) Filed: Nov. 15, 2013

(65) Prior Publication Data

US 2014/0142278 A1    May 22, 2014

Related U.S. Application Data

(62) Division of application No. 12/373,470, filed as application No. PCT/US2007/073455 on Jul. 13, 2007, now Pat. No. 8,586,330.

(60) Provisional application No. 60/831,152, filed on Jul. 14, 2006.

(51) Int. Cl.

| C07K 7/00 | (2006.01) |
|---|---|
| C12N 9/20 | (2006.01) |
| C07K 14/37 | (2006.01) |
| C12N 15/62 | (2006.01) |
| C12N 15/81 | (2006.01) |
| C12P 21/02 | (2006.01) |
| A61K 38/00 | (2006.01) |

(52) U.S. Cl.
CPC . *C07K 14/37* (2013.01); *C12N 9/20* (2013.01); *C12N 15/625* (2013.01); *C12N 15/81* (2013.01); *C12P 21/02* (2013.01); *C07K 2319/02* (2013.01)

(58) Field of Classification Search
None
See application file for complete search history.

(56) References Cited

U.S. PATENT DOCUMENTS

| 5,705,358 | A | 1/1998 | Gouka et al. |
|---|---|---|---|
| 5,766,912 | A | 6/1998 | Boel et al. |
| 5,869,438 | A | 2/1999 | Svendsen et al. |
| 5,892,013 | A * | 4/1999 | Svendsen et al. ............ 536/23.2 |
| 6,410,272 | B1 | 6/2002 | Meyhack et al. |
| 6,495,357 | B1 | 12/2002 | Fuglsang et al. |
| 7,157,262 | B2 | 1/2007 | Fuglsang et al. |
| 7,396,657 | B2 * | 7/2008 | Munk et al. ..................... 435/18 |
| 2003/0148441 | A1 | 8/2003 | Okkels |
| 2004/0259210 | A1 | 12/2004 | Humphreys |
| 2008/0214411 | A1 | 9/2008 | Gray et al. |
| 2009/0011995 | A1 | 1/2009 | Lee et al. |

FOREIGN PATENT DOCUMENTS

| WO | 9522615 A1 | 8/1995 |
|---|---|---|
| WO | 9704079 A1 | 2/1997 |
| WO | 02066622 A2 | 8/2002 |

OTHER PUBLICATIONS

Belin et al., "Functionality activity of eukaryotic signal sequences in *Escherichia coli*: the Ovalbumin Family of serine protease inhibitors", 2004, Journal of Molecular Biology 335: 437-453.
Tsuchiya et al., "Gene design of signal sequence for effective secretion of protein", 2003, Nucleic Acids Research Supplement No. 3, pp. 262-262.
Nothwehr and Gordon, "Structural features in the NH2-terminal region of a model eukaryotic signal peptide influence the site of its cleavage by signal peptidase", 1990, The Journal of Biological Chemistry 265: 17202-17208.
Ngsee and Smith, "Changes in a mammalian signal sequence required for efficient protein secretion by yeast", 1990, Gene 86: 251-255.
Muller et al, 1998, GenBank Access No. AF054513.
Boet et al, 1998—Swiss-Prot Access No. 059952.
Fungus, Wikipedia, 2011, 1-35.
Ordaz et al, 2004, IUBMB ASBMB 2004 Meeting Abstract C87.
Zhang et al, 1996, Amino Acids 10, 253-262.
Zhou et al, 1993, Biofactors 4(2), 105-115.
WO 1997-004079 A1—Seq Alingment.
WO 2008-008967—Seq Alignment I.
WO 2008-008967—Seq Alignment II.

* cited by examiner

*Primary Examiner* — Anand Desai
*Assistant Examiner* — Samuel Liu
(74) *Attorney, Agent, or Firm* — Robert Starnes

(57) ABSTRACT

The present invention relates to methods for producing a polypeptide having biological activity, comprising: (a) cultivating a fungal host cell in a medium conducive for the production of the polypeptide, wherein the fungal host cell comprises a first polynucleotide encoding the polypeptide operably linked to a second polynucleotide encoding a variant signal peptide or a variant prepropeptide; and (b) isolating the secreted polypeptide having biological activity from the cultivation medium.

15 Claims, 21 Drawing Sheets

SEQUENCE LISTING

<160> NUMBER OF SEQ ID NOS: 36

<210> SEQ ID NO 1
<211> LENGTH: 66
<212> TYPE: DNA
<213> ORGANISM: Thermomyces lanuginosus

<400> SEQUENCE: 1

```
atgaggagct cccttgtgct gttctttgtc tctgcgtgga cggccttggc cagtcctatt    60
cgtcga                                                                66
```

```
<210> SEQ ID NO 2
<211> LENGTH: 22
<212> TYPE: PRT
<213> ORGANISM: Thermomyces lanuginosus

<400> SEQUENCE: 2

Met Arg Ser Ser Leu Val Leu Phe Phe Val Ser Ala Trp Thr Ala Leu
1               5                   10                  15

Ala Ser Pro Ile Arg Arg
            20

<210> SEQ ID NO 3
<211> LENGTH: 51
<212> TYPE: DNA
<213> ORGANISM: Thermomyces lanuginosus

<400> SEQUENCE: 3
atgaagagct cccttgtgct gttctttgtc tctgcgtgga cggccttggc c          51

<210> SEQ ID NO 4
<211> LENGTH: 17
<212> TYPE: PRT
<213> ORGANISM: Thermomyces lanuginosus

<400> SEQUENCE: 4

Met Lys Ser Ser Leu Val Leu Phe Phe Val Ser Ala Trp Thr Ala Leu
1               5                   10                  15

Ala

<210> SEQ ID NO 5
<211> LENGTH: 66
<212> TYPE: DNA
<213> ORGANISM: Thermomyces lanuginosus

<400> SEQUENCE: 5
atgaagagct cccttgtgct gttctttgtc tctgcgtgga cggccttggc cagtcctatt    60
cgtcga                                                               66

<210> SEQ ID NO 6
<211> LENGTH: 22
<212> TYPE: PRT
<213> ORGANISM: Thermomyces lanuginosus

<400> SEQUENCE: 6

Met Lys Ser Ser Leu Val Leu Phe Phe Val Ser Ala Trp Thr Ala Leu
1               5                   10                  15

Ala Ser Pro Ile Arg Arg
            20

<210> SEQ ID NO 7
<211> LENGTH: 918
<212> TYPE: DNA
<213> ORGANISM: Thermomyces lanuginosus

<400> SEQUENCE: 7
atgaggagct cccttgtgct gttctttgtc tctgcgtgga cggccttggc cagtcctatt    60
cgtcgagagg tctcgcagga tctgtttaac cagttcaatc tctttgcaca gtattctgca   120
gccgcatact gcggaaaaaa caatgatgcc ccagctggta caaacattac gtgcacggga   180
aatgcctgcc ccgaggtaga aaggcggat gcaacgtttc tctactcgtt tgaagactct   240
ggagtgggcg atgtcaccgg cttccttgct ctcgacaaca cgaacaaatt gatcgtcctc   300
```

```
tctttccgtg gctctcgttc catagagaac tggatcggga atcttaactt cgacttgaaa    360
gaaataaatg acatttgctc cggctgcagg ggacatgacg gcttcacttc gtcctggagg    420
tctgtagccg atacgttaag gcagaaggtg gaggatgctg tgagggagca tcccgactat    480
cgcgtggtgt ttaccggaca tagcttgggt ggtgcattgg caactgttgc cggagcagac    540
ctgcgtggaa atgggtatga tatcgacgtg ttttcatatg gcgcccccg agtcggaaac     600
agggcttttg cagaattcct gaccgtacag accggcggaa cactctaccg cattacccac    660
accaatgata ttgtccctag actcccgccg cgcgaattcg gttacagcca ttctagccca    720
gagtactgga tcaaatctgg aaccttgtc cccgtcaccc gaaacgatat cgtgaagata     780
gaaggcatcg atgccaccgg cggcaataac cagcctaaca ttccggatat ccctgcgcac    840
ctatggtact cgggttaat tgggacatgt ctttagtggc cggcgcggct gggtccgact     900
ctagcgagct cgagatct                                                  918
```

<210> SEQ ID NO 8
<211> LENGTH: 291
<212> TYPE: PRT
<213> ORGANISM: Thermomyces lanuginosus

<400> SEQUENCE: 8

```
Met Arg Ser Ser Leu Val Leu Phe Phe Val Ser Ala Trp Thr Ala Leu
1               5                   10                  15

Ala Ser Pro Ile Arg Arg Glu Val Ser Gln Asp Leu Phe Asn Gln Phe
            20                  25                  30

Asn Leu Phe Ala Gln Tyr Ser Ala Ala Tyr Cys Gly Lys Asn Asn
        35                  40                  45

Asp Ala Pro Ala Gly Thr Asn Ile Thr Cys Thr Gly Asn Ala Cys Pro
    50                  55                  60

Glu Val Glu Lys Ala Asp Ala Thr Phe Leu Tyr Ser Phe Glu Asp Ser
65                  70                  75                  80

Gly Val Gly Asp Val Thr Gly Phe Leu Ala Leu Asp Asn Thr Asn Lys
                85                  90                  95

Leu Ile Val Leu Ser Phe Arg Gly Ser Arg Ser Ile Glu Asn Trp Ile
            100                 105                 110

Gly Asn Leu Asn Phe Asp Leu Lys Glu Ile Asn Asp Ile Cys Ser Gly
        115                 120                 125

Cys Arg Gly His Asp Gly Phe Thr Ser Ser Trp Arg Ser Val Ala Asp
    130                 135                 140

Thr Leu Arg Gln Lys Val Glu Asp Ala Val Arg Glu His Pro Asp Tyr
145                 150                 155                 160

Arg Val Val Phe Thr Gly His Ser Leu Gly Gly Ala Leu Ala Thr Val
                165                 170                 175

Ala Gly Ala Asp Leu Arg Gly Asn Gly Tyr Asp Ile Asp Val Phe Ser
            180                 185                 190

Tyr Gly Ala Pro Arg Val Gly Asn Arg Ala Phe Ala Glu Phe Leu Thr
        195                 200                 205

Val Gln Thr Gly Gly Thr Leu Tyr Arg Ile Thr His Thr Asn Asp Ile
    210                 215                 220

Val Pro Arg Leu Pro Pro Arg Glu Phe Gly Tyr Ser His Ser Ser Pro
225                 230                 235                 240

Glu Tyr Trp Ile Lys Ser Gly Thr Leu Val Pro Val Thr Arg Asn Asp
                245                 250                 255
```

```
Ile Val Lys Ile Glu Gly Ile Asp Ala Thr Gly Gly Asn Asn Gln Pro
            260                 265                 270

Asn Ile Pro Asp Ile Pro Ala His Leu Trp Tyr Phe Gly Leu Ile Gly
        275                 280                 285

Thr Cys Leu
    290

<210> SEQ ID NO 9
<211> LENGTH: 873
<212> TYPE: DNA
<213> ORGANISM: Thermomyces lanuginosus

<400> SEQUENCE: 9
atgaggagct cccttgtgct gttctttgtc tctgcgtgga cggccttggc cagtcctatt    60
cgtcgagagg tctcgcagga tctgtttaac cagttcaatc tctttgcaca gtattctgca   120
gccgcatact gcggaaaaaa caatgatgcc ccagctggta caaacattac gtgcacggga   180
aatgcctgcc ccgaggtaga gaaggcggat gcaacgtttc tctactcgtt tgaagactct   240
ggagtgggcg atgtcaccgg cttccttgct ctcgacaaca cgaacaaatt gatcgtcctc   300
tctttccgtg gctctcgttc catagagaac tggatcggga tcttaacttc gacttgaaa   360 gaaataaatg acatttgctc cggctgcagg ggacatgacg gcttcacttc gtcctggagg   420
tctgtagccg atacgttaag gcagaaggtg gaggatgctg tgagggagca tcccgactat   480
cgcgtggtgt ttaccggaca tagcttgggt ggtgcattgg caactgttgc cggagcagac   540
ctgcgtggaa atgggtatga tatcgacgtg ttttcatatg cgcccccccg agtcggaaac   600
agggcttttg cagaattcct gaccgtacag accggcggaa cactctaccg cattacccac   660
accaatgata ttgtccctag actcccgccg cgcgaattcg gttacagcca ttctagccca   720
gaatactgga tcaaatctgg aacccttgtc ccgtccggc gacgagacat cgtgaagata   780
gaaggcatcg atgccaccgg cggcaataac cagcctaaca ttccggatat ccctgcgcac   840
ctatggtact cgggttaat tgggacatgt ctt                                 873

<210> SEQ ID NO 10
<211> LENGTH: 291
<212> TYPE: PRT
<213> ORGANISM: Thermomyces lanuginosus

<400> SEQUENCE: 10

Met Arg Ser Ser Leu Val Leu Phe Phe Val Ser Ala Trp Thr Ala Leu
1               5                   10                  15

Ala Ser Pro Ile Arg Arg Glu Val Ser Gln Asp Leu Phe Asn Gln Phe
            20                  25                  30

Asn Leu Phe Ala Gln Tyr Ser Ala Ala Ala Tyr Cys Gly Lys Asn Asn
        35                  40                  45

Asp Ala Pro Ala Gly Thr Asn Ile Thr Cys Thr Gly Asn Ala Cys Pro
    50                  55                  60

Glu Val Glu Lys Ala Asp Ala Thr Phe Leu Tyr Ser Phe Glu Asp Ser
65                  70                  75                  80

Gly Val Gly Asp Val Thr Gly Phe Leu Ala Leu Asp Asn Thr Asn Lys
                85                  90                  95

Leu Ile Val Leu Ser Phe Arg Gly Ser Arg Ser Ile Glu Asn Trp Ile
            100                 105                 110

Gly Asn Leu Asn Phe Asp Leu Lys Glu Ile Asn Asp Ile Cys Ser Gly
        115                 120                 125
```

```
            Cys Arg Gly His Asp Gly Phe Thr Ser Ser Trp Arg Ser Val Ala Asp
            130                 135                 140
            Thr Leu Arg Gln Lys Val Glu Asp Ala Val Arg Glu His Pro Asp Tyr
            145                 150                 155                 160
            Arg Val Val Phe Thr Gly His Ser Leu Gly Gly Ala Leu Ala Thr Val
                            165                 170                 175
            Ala Gly Ala Asp Leu Arg Gly Asn Gly Tyr Asp Ile Asp Val Phe Ser
                        180                 185                 190
            Tyr Gly Ala Pro Arg Val Gly Asn Arg Ala Phe Ala Glu Phe Leu Thr
                    195                 200                 205
            Val Gln Thr Gly Gly Thr Leu Tyr Arg Ile Thr His Thr Asn Asp Ile
            210                 215                 220
            Val Pro Arg Leu Pro Pro Arg Glu Phe Gly Tyr Ser His Ser Ser Pro
            225                 230                 235                 240
            Glu Tyr Trp Ile Lys Ser Gly Thr Leu Val Pro Val Arg Arg Arg Asp
                            245                 250                 255
            Ile Val Lys Ile Glu Gly Ile Asp Ala Thr Gly Gly Asn Asn Gln Pro
                        260                 265                 270
            Asn Ile Pro Asp Ile Pro Ala His Leu Trp Tyr Phe Gly Leu Ile Gly
                    275                 280                 285
            Thr Cys Leu
                290

<210> SEQ ID NO 11
<211> LENGTH: 36
<212> TYPE: DNA
<213> ORGANISM: Saccharomyces cerevisiae

<400> SEQUENCE: 11
caccggtgca tgcctgcagg agctcctagt tagaaa                                36

<210> SEQ ID NO 12
<211> LENGTH: 36
<212> TYPE: DNA
<213> ORGANISM: Saccharomyces cerevisiae

<400> SEQUENCE: 12
aactattctt gaatggaatt ctagtcgatg acttct                                36

<210> SEQ ID NO 13
<211> LENGTH: 26
<212> TYPE: DNA
<213> ORGANISM: Saccharomyces cerevisiae

<400> SEQUENCE: 13
tctagagggc cgcatcatgt aattag                                           26

<210> SEQ ID NO 14
<211> LENGTH: 30
<212> TYPE: DNA
<213> ORGANISM: Saccharomyces cerevisiae

<400> SEQUENCE: 14
gacgccatgg tgaagctttc ttttaatcgt                                       30

<210> SEQ ID NO 15
<211> LENGTH: 95
<212> TYPE: DNA
<213> ORGANISM: Thermomyces lanuginosus
```

<400> SEQUENCE: 15
caagaagatt acaaactatc aatttcatac acaatataaa cgattaaaag aaagcttcac    60
catgaggagc tcccttgtgc tgttctttgt ctctg    95

<210> SEQ ID NO 16
<211> LENGTH: 87
<212> TYPE: DNA
<213> ORGANISM: Thermomyces lanuginosus

<400> SEQUENCE: 16
gagggcgtga atgtaagcgt gacataacta attacatgat gcggccctct agattatcaa    60
agacatgtcc caattaaccc gaagtac    87

<210> SEQ ID NO 17
<211> LENGTH: 95
<212> TYPE: DNA
<213> ORGANISM: Thermomyces lanuginosus

<400> SEQUENCE: 17
caagaagatt acaaactatc aatttcatac acaatataaa cgattaaaag aaagcttcac    60
catgaggagc tcccttgtgc tgttctttgt ctctg    95

<210> SEQ ID NO 18
<211> LENGTH: 87
<212> TYPE: DNA
<213> ORGANISM: Thermomyces lanuginosus

<400> SEQUENCE: 18
gagggcgtga atgtaagcgt gacataacta attacatgat gcggccctct agattatcaa    60
agacatgtcc caattaaccc gaagtac    87

<210> SEQ ID NO 19
<211> LENGTH: 46
<212> TYPE: DNA
<213> ORGANISM: Thermomyces lanuginosus

<400> SEQUENCE: 19
ctctgcgtgg acggccttgg ccgaggtctc gcaggatctg tttaac    46

<210> SEQ ID NO 20
<211> LENGTH: 45
<212> TYPE: DNA
<213> ORGANISM: Thermomyces lanuginosus

<400> SEQUENCE: 20
ttaaacagat cctgcgagac ctcggccaag gccgtccacg cagag    45

<210> SEQ ID NO 21
<211> LENGTH: 26
<212> TYPE: DNA
<213> ORGANISM: Thermomyces lanuginosus

<400> SEQUENCE: 21
ctaggaaccc atcaggttgg tggaag    26

<210> SEQ ID NO 22
<211> LENGTH: 114
<212> TYPE: DNA
<213> ORGANISM: Thermomyces lanuginosus

```
<220> FEATURE:
<221> NAME/KEY: misc_feature
<222> LOCATION: (40)..(93)
<223> OTHER INFORMATION: N = A, C, G, OR T

<400> SEQUENCE: 22
ctgtgcaaag agattgaact ggttaaacag atcctgcgan nnnnnnnnnn nnnnnnnnnn    60
nnnnnnnnnn nnnnnnnnnn nnnnnnnnnn nnncatggtg aagctttctt ttaa         114

<210> SEQ ID NO 23
<211> LENGTH: 36
<212> TYPE: DNA
<213> ORGANISM: Thermomyces lanuginosus

<400> SEQUENCE: 23
acacaactgg ccatgaggag ctcccttgtg ctgttc                              36

<210> SEQ ID NO 24
<211> LENGTH: 40
<212> TYPE: DNA
<213> ORGANISM: Thermomyces lanuginosus

<400> SEQUENCE: 24
agtcacctct agttaattaa ttatcaaata catgtcccaa                          40

<210> SEQ ID NO 25
<211> LENGTH: 26
<212> TYPE: DNA
<213> ORGANISM: Aspergillus niger

<400> SEQUENCE: 25
gtcgacatgg tgttttgatc atttta                                        26

<210> SEQ ID NO 26
<211> LENGTH: 26
<212> TYPE: DNA
<213> ORGANISM: Aspergillus niger

<400> SEQUENCE: 26
ccatggccag ttgtgtatat agagga                                        26

<210> SEQ ID NO 27
<211> LENGTH: 36
<212> TYPE: DNA
<213> ORGANISM: Thermomyces lanuginosus

<400> SEQUENCE: 27
acacaactgg ccatgaggag ctcccttgtg ctgttc                              36

<210> SEQ ID NO 28
<211> LENGTH: 47
<212> TYPE: DNA
<213> ORGANISM: Thermomyces lanuginosus

<400> SEQUENCE: 28
agtcacctct agttaattaa ttatcaaaga catgtcccaa ttaaccc                  47

<210> SEQ ID NO 29
<211> LENGTH: 44
<212> TYPE: DNA
<213> ORGANISM: Thermomyces lanuginosus
```

```
<400> SEQUENCE: 29
ctctatatac acaactggcc atgaagagct cccttgtgct gttc                    44

<210> SEQ ID NO 30
<211> LENGTH: 47
<212> TYPE: DNA
<213> ORGANISM: Thermomyces lanuginosus

<400> SEQUENCE: 30
caggtgtcag tcacctctag ttatcaaaga catgtcccaa ttaaccc                 47

<210> SEQ ID NO 31
<211> LENGTH: 29
<212> TYPE: DNA
<213> ORGANISM: Thermomyces lanuginosus

<400> SEQUENCE: 31
cacaactggc catgaagagc tcccttgtg                                     29

<210> SEQ ID NO 32
<211> LENGTH: 29
<212> TYPE: DNA
<213> ORGANISM: Thermomyces lanuginosus

<400> SEQUENCE: 32
cacaagggag ctcttcatgg ccagttgtg                                     29

<210> SEQ ID NO 33
<211> LENGTH: 26
<212> TYPE: DNA
<213> ORGANISM: Thermomyces lanuginosus

<400> SEQUENCE: 33
atactggcaa gggatgccat gcttgg                                        26

<210> SEQ ID NO 34
<211> LENGTH: 29
<212> TYPE: DNA
<213> ORGANISM: Thermomyces lanuginosus

<400> SEQUENCE: 34
cacaactggc catgaggagc tcccttgtg                                     29

<210> SEQ ID NO 35
<211> LENGTH: 29
<212> TYPE: DNA
<213> ORGANISM: Thermomyces lanuginosus

<400> SEQUENCE: 35
cacaagggag ctcctcatgg ccagttgtg                                     29

<210> SEQ ID NO 36
<211> LENGTH: 5
<212> TYPE: PRT
<213> ORGANISM: Thermomyces lanuginosus

<400> SEQUENCE: 36

Ser Pro Ile Arg Arg
1               5
```

US 9,273,104 B2

METHODS FOR PRODUCING SECRETED POLYPEPTIDES HAVING BIOLOGICAL ACTIVITY

CROSS-REFERENCE TO RELATED APPLICATIONS

This application is a divisional application of U.S. application Ser. No. 12/373,470 filed on Mar. 10, 2009, now U.S. Pat. No. 8,586,330, which is a 35 U.S.C. 371 national application of PCT/US07/73455 filed on Jul. 13, 2007, which claims priority or the benefit under 35 U.S.C. 119 of U.S. Provisional Application Ser. No. 60/831,152 filed on Jul. 14, 2006, the contents of which are fully incorporated herein by reference.

BACKGROUND OF THE INVENTION

1. Field of the Invention

The present invention relates to methods for producing secreted polypeptides. The present invention also relates to variant signal peptides or variant prepropeptides and nucleic acid constructs, vectors, and host cells comprising the variant signal peptide or variant prepropeptide coding sequences operably linked to polynucleotides encoding polypeptides.

2. Description of the Related Art

A signal peptide is an amino acid sequence linked in frame to the amino terminus of a polypeptide having biological activity and directs the encoded polypeptide into the cell's secretory pathway. A propeptide is an amino acid sequence positioned at the amino terminus of a polypeptide, wherein the resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. Where both signal peptide and propeptide regions are present at the amino terminus of a polypeptide, the propeptide region is linked in frame to the amino terminus of a polypeptide and the signal peptide region is linked in frame to the amino terminus of the propeptide region.

The secretion of a recombinant polypeptide of interest in a particular host cell may require the replacement of its native signal peptide with a new signal peptide that is compatible with the host cell of choice. In addition, a propeptide sequence of a polypeptide may also need to be replaced with a different propeptide sequence or deleted because the propeptide sequence is not processed or is processed improperly by the host cell to secrete an active polypeptide. In other cases, a signal peptide and/or propeptide may be absent.

It may be possible to improve the secretion of a polypeptide of interest by modifying the native signal peptide or native prepropeptide naturally associated with the polypeptide through mutation.

Belin et al., 2004, *Journal of Molecular Biology* 335: 437-453, describe mutations that improve the functional activity of the plasminogen activator inhibitor 2 (PAI-2) signal sequence. Tsuchiya et al., 2003, *Nucleic Acids Research Supplement No. 3*, pp. 262-262, describe mutation of a signal sequence for effective secretion of human lysozyme in yeast. Nothwehr and Gordon, 1990, *The Journal of Biological Chemistry* 265: 17202-17208, describe structural features in the amino terminal region of the human pre(Δpro)apolipoprotein A-II signal peptide that influences the site of its cleavage by signal peptidase. Ngsee and Smith, 1990, *Gene* 86: 251-255, describe changes in the bovine prolactin signal peptide required for efficient secretion in yeasts.

U.S. Pat. No. 5,766,912 discloses the cloning and sequence of a full-length wild-type lipase from *Thermomyces lanuginosus* containing a prepropeptide sequence. U.S. Pat. No. 5,869,438 discloses variants of a full-length wild-type lipase from *Thermomyces lanuginosus*.

There is a need in the art for improved signal peptide and propeptide sequences for the secretion of active polypeptides in various host cells.

It is an object of the present invention to provide improved methods for producing a polypeptide in a fungal host cell using variant signal peptides or variant prepropeptides.

SUMMARY OF THE INVENTION

The present invention relates to methods for producing a secreted polypeptide having biological activity, comprising:

(a) cultivating a fungal host cell in a medium conducive for the production of the polypeptide, wherein the fungal host cell comprises a first polynucleotide encoding the polypeptide operably linked to a second polynucleotide encoding a variant signal peptide or a variant prepropeptide selected from the group consisting of:

(i) a variant of a parent signal peptide comprising a substitution at a position corresponding to position 2 of amino acids 1 to 17 of SEQ ID NO: 2, wherein the variant signal peptide is linked in frame to the amino terminus of the polypeptide;

(ii) a variant of a parent prepropeptide comprising a deletion at one or more (several) positions corresponding to positions 18, 19, 20, 21, and 22 of amino acids 1 to 22 of SEQ ID NO: 2, wherein the variant peptide is linked in frame to the amino terminus of the polypeptide;

(iii) a variant of a parent prepropeptide comprising a substitution at a position corresponding to position 2 of amino acids 1 to 22 of SEQ ID NO: 2, wherein the variant prepropeptide is linked in frame to the amino terminus of the polypeptide; and (iv) a variant of a parent prepropeptide comprising a substitution at a position corresponding to position 2 of amino acids 1 to 22 of SEQ ID NO: 2 and a deletion at one or more (several) positions corresponding to positions 18, 19, 20, 21, and 22 of amino acids 1 to 22 of SEQ ID NO: 2; and (b) isolating the secreted polypeptide having biological activity from the cultivation medium.

The present invention also relates to isolated polynucleotides encoding variant signal peptides and variant prepropeptides and to constructs, vectors, and fungal host cells comprising the polynucleotides encoding the variant signal peptides and variant prepropeptides operably linked to polynucleotides encoding polypeptides.

BRIEF DESCRIPTION OF THE FIGURES

FIG. 1 shows a restriction map of pBM128a.
FIG. 3 shows a restriction map of pBM126a.

FIG. 16 shows a restriction map of pBM120a.

DEFINITIONS

Figure 1:
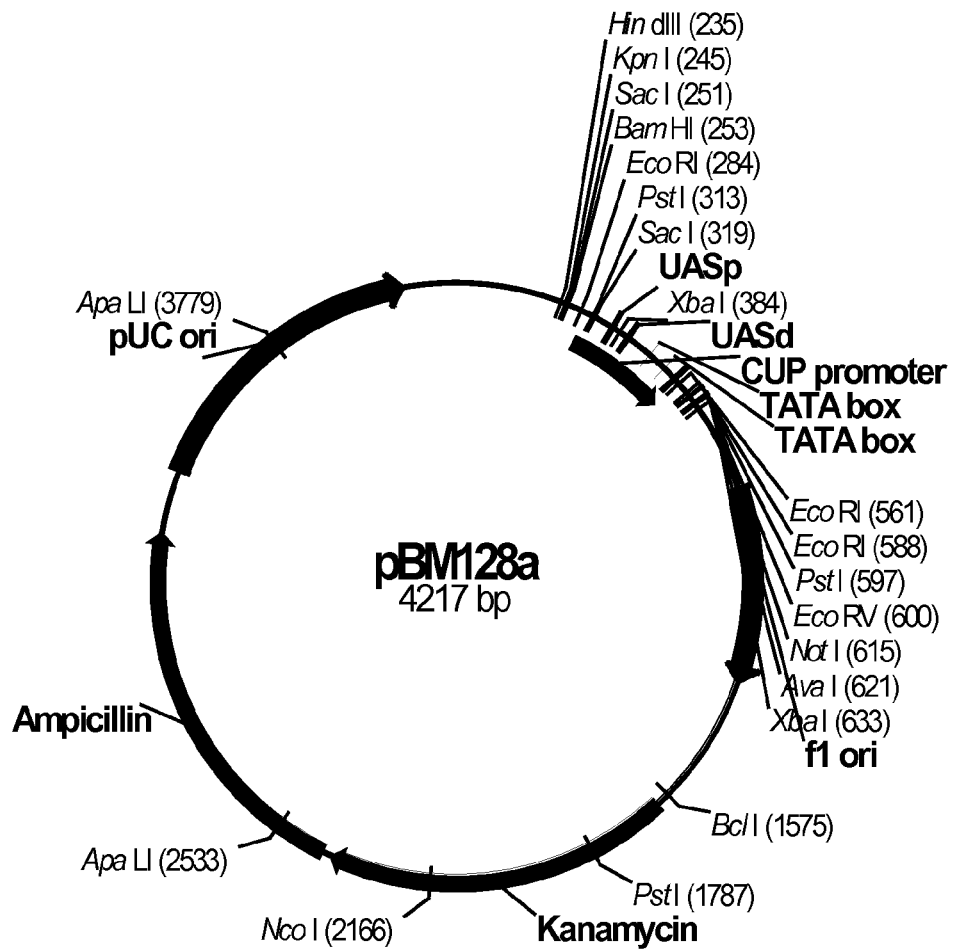

Full-length polypeptide: The term "full-length polypeptide" is defined herein as a precursor form of a polypeptide having biological activity, wherein the precursor contains a signal peptide and alternatively also a propeptide, wherein upon secretion from a cell, the signal peptide is cleaved and alternatively also the propeptide is cleaved yielding a polypeptide with biological activity.

Signal peptide: The term "signal peptide" is defined herein as a peptide linked (fused) in frame to the amino terminus of a polypeptide having biological activity and directs the polypeptide into the cell's secretory pathway. A propeptide may be present between the signal peptide and the amino terminus of the polypeptide (see prepropeptide definition below).

Propeptide: The term "propeptide" is an amino acid sequence linked (fused) in frame to the amino terminus of a polypeptide, wherein the resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide.

Prepropeptide: The term "prepropeptide" is defined herein as a signal peptide and propeptide present at the amino terminus of a polypeptide, where the propeptide is linked (or fused) in frame to the amino terminus of a polypeptide and the signal peptide region is linked in frame (or fused) to the amino terminus of the propeptide region.

Signal peptide coding sequence: The term "signal peptide coding sequence" is defined herein as a polynucleootide that encodes a signal peptide.

Propeptide coding sequence: The term "propeptide coding sequence" is defined herein as a polynucleootide that encodes a propeptide.

Prepropeptide coding sequence: The term "prepropeptide coding sequence" is defined herein as a polynucleootide that encodes a prepropeptide.

Wild-type signal peptide: The term "wild-type signal peptide" denotes a signal peptide expressed by a naturally occurring microorganism, such as a yeast or filamentous fungus found in nature.

Parent signal peptide: The term "parent signal peptide" as used herein means a signal peptide to which modifications, e.g., substitution(s), insertion(s), deletion(s), and/or truncation(s), are made to produce a signal peptide variant of the present invention. This term also refers to the signal peptide with which a variant is compared and aligned. The parent may be a naturally occurring (wild-type) signal peptide, or it may even be a variant thereof, prepared by any suitable means. For instance, the parent signal peptide may be a variant of a naturally occurring signal peptide which has been modified or altered in the amino acid sequence. A parent signal peptide may also be an allelic variant which is a signal peptide encoded by any of two or more alternative forms of a polynucleotide sequence occupying the same chromosomal locus.

Wild-type prepropeptide: The term "wild-type prepropeptide" denotes a prepropeptide expressed by a naturally occurring microorganism, such as a yeast or filamentous fungus found in nature.

Parent prepropeptide: The term "parent prepropeptide" as used herein means a prepropeptide to which modifications, e.g., substitution(s), insertion(s), deletion(s), and/or truncation(s), are made to produce a prepropeptide variant of the present invention. This term also refers to the prepropeptide with which a variant is compared and aligned. The parent may be a naturally occurring (wild-type) prepropeptide, or it may even be a variant thereof, prepared by any suitable means. For instance, the parent prepropeptide may be a variant of a naturally occurring prepropeptide which has been modified or altered in the amino acid sequence. A parent prepropeptide may also be an allelic variant which is a prepropeptide encoded by any of two or more alternative forms of a polynucleotide sequence occupying the same chromosomal locus.

Variant: The term "variant" is defined herein as a peptide or polypeptide comprising one or more (several) alterations, such as substitutions, insertions, deletions, and/or truncations of one or more (several) specific amino acid residues at one or more (several) specific positions in the peptide or polypeptide.

Variant signal peptide: The term "variant signal peptide" is defined herein as a signal peptide of a parent signal peptide, wherein the variant signal peptide comprises one or more (several) alterations, such as substitutions, insertions, deletions, and/or truncations of one or more (several) specific amino acid residues at one or more (several) specific positions in the signal peptide.

Variant prepropeptide: The term "variant prepropeptide" is defined herein as a prepropeptide of a parent prepropeptide, wherein the variant prepropeptide comprises one or more (several) alterations, such as substitutions, insertions, deletions, and/or truncations of one or more (several) specific amino acid residues at one or more (several) specific positions in the prepropeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Coding sequence: The term "coding sequence" is defined herein as a polynucleotide sequence that is transcribed into mRNA which is translated into a polypeptide when placed under the control of the appropriate control sequences. The boundaries of the coding sequence are generally determined by the start codon located at the beginning of the open reading frame of the 5' end of the mRNA and a stop codon located at the 3' end of the open reading frame of the mRNA. A coding sequence can include, but is not limited to, genomic DNA, cDNA, semisynthetic, synthetic, and recombinant nucleotide sequences.

The 5' end of the polypeptide coding sequence may contain a native signal peptide coding region or a native prepropeptide coding region naturally linked in translation reading frame with the segment of the coding region which encodes the polypeptide. Alternatively, the 5' end of the polypeptide coding sequence may lack a native signal peptide coding region or a native prepropeptide coding region.

Mature polypeptide: The term "mature polypeptide" is defined herein as a polypeptide having biological activity that is in its final form following translation and any post-translational modifications, such as N-terminal processing, C-terminal truncation, glycosylation, phosphorylation, etc.

Mature polypeptide coding sequence: The term "mature polypeptide coding sequence" is defined herein as a polynucleotide sequence that encodes a mature polypeptide having biological activity.

DETAILED DESCRIPTION OF THE INVENTION

The present invention relates to methods for producing a polypeptide having biological activity, comprising: (a) cultivating a fungal host cell in a medium conducive for the production of the polypeptide, wherein the fungal host cell comprises a first polynucleotide encoding the polypeptide operably linked to a second polynucleotide encoding a variant signal peptide or a variant prepropeptide selected from the group consisting of: (i) a variant of a parent signal peptide comprising a substitution at a position corresponding to position 2 of amino acids 1 to 17 of SEQ ID NO: 2, wherein the variant signal peptide is linked in frame to the amino terminus of the polypeptide; (ii) a variant of a parent prepropeptide comprising a deletion at one or more (several) positions corresponding to positions 18, 19, 20, 21, and 22 of amino acids 1 to 22 of SEQ ID NO: 2, wherein the variant peptide is linked in frame to the amino terminus of the polypeptide; (iii) a variant of a parent prepropeptide comprising a substitution at a position corresponding to position 2 of amino acids 1 to 12 of SEQ ID NO: 2, wherein the variant prepropeptide is linked in frame to the amino terminus of the polypeptide; and (iv) a variant of a parent prepropeptide comprising a substitution at a position corresponding to position 2 of amino acids 1 to 22 of SEQ ID NO: 2 and a deletion at one or more (several) positions corresponding to positions 18, 19, 20, 21, and 22 of amino acids 1 to 22 of SEQ ID NO: 2; and (b) isolating the secreted polypeptide having biological activity from the cultivation medium.

In the production methods of the present invention, the fungal host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection).

The polypeptides having biological activity may be detected using methods known in the art that are specific for the polypeptides. These detection methods may include use of specific antibodies, high performance liquid chromatography, capillary chromatography, formation of an enzyme product, disappearance of an enzyme substrate, or SDS-PAGE. For example, where the polypeptide is an enzyme, an enzyme assay may be used to determine the activity of the enzyme. Procedures for determining enzyme activity are known in the art for many enzymes (see, for example, D. Schomburg and M. Salzmann (eds.), *Enzyme Handbook*, Springer-Verlag, New York, 1990).

In the methods of the present invention, the fungal cell preferably produces at least about 25% more, more preferably at least about 50% more, more preferably at least about 75% more, more preferably at least about 100% more, even more preferably at least about 200% more, most preferably at least about 300% more, and even most preferably at least about 400% more polypeptide relative to a fungal cell containing a native signal peptide coding sequence or a native prepropeptide coding sequence operably linked to a polynucleotide sequence encoding the polypeptide when cultured under identical production conditions.

The resulting secreted and activated polypeptide can be recovered directly from the medium by methods known in the art. For example, the polypeptide may be recovered from the nutrient medium by conventional procedures including, but not limited to, centrifugation, filtration, extraction, spray-drying, evaporation, or precipitation.

The polypeptides having biological activity can be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Conventions for Designation of Variants

In the present invention, a specific numbering of amino acid residue positions is employed in the signal peptide variants and prepropeptide variants. For example, by aligning the amino acid sequences of known signal peptide or prepropeptide sequences, it is possible to designate an amino acid position number to any amino acid residue in any signal peptide or prepropeptide sequence.

For example, using the numbering system originating from the amino acid sequence of the lipase disclosed in SEQ ID NO: 2, aligned with the amino acid sequence of a number of other lipases or other enzymes, it is possible to indicate the position of an amino acid residue in regions of structural homology in the signal peptide or prepropeptide region.

Multiple alignments of protein sequences may be made, for example, using "ClustalW" (Thompson, J. D., Higgins, D. G. and Gibson, T. J., 1994, CLUSTAL W: Improving the sensitivity of progressive multiple sequence alignment through sequence weighting, positions-specific gap penalties and weight matrix choice, *Nucleic Acids Research* 22: 4673-4680). Multiple alignments of DNA sequences may be done using the protein alignment as a template, replacing the amino acids with the corresponding codon from the DNA sequence.

Pairwise sequence comparison algorithms in common use are adequate to detect similarities between protein sequences that have not diverged beyond the point of approximately 20-30% sequence identity (Doolittle, 1992, *Protein Sci.* 1: 191-200; Brenner et al., 1998, *Proc. Natl. Acad. Sci. USA* 95, 6073-6078). However, truly homologous proteins with the same fold and similar biological function have often diverged to the point where traditional sequence-based comparisons fail to detect their relationship (Lindahl and Elofsson, 2000, *J. Mol. Biol.* 295: 613-615). Greater sensitivity in sequence-based searching can be attained using search programs that utilize probabilistic representations of protein families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the protein of interest has one or more representatives in the protein structure databases. Programs such as GenTHREADER (Jones 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the Structural Classification of Proteins (SCOP) database. These alignments can in turn be used to generate homology models for the protein of interest, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. These alignments can be used to predict the structurally and functionally corresponding amino acid residues in proteins within the same structural superfamily. This information, along with information derived from homology modeling and profile searches, can be used to predict which residues to mutate when moving mutations of interest from one protein to a close or remote homolog.

In describing the various signal peptide variants or prepropeptide variants of the present invention, the nomenclature described below is adapted for ease of reference. In all cases, the accepted IUPAC single letter or triple letter amino acid abbreviation is employed.

Substitutions. For an amino acid substitution, the following nomenclature is used: Original amino acid, position, substituted amino acid. Accordingly, the substitution of arginine with lysine at position 2 is designated as "Arg2Lys" or "R2K".

Deletions. For an amino acid deletion, the following nomenclature is used: Original amino acid, position*. Accordingly, the deletion of serine at position 18 is designated as "Ser18*" or "S18*".

Insertions. For an amino acid insertion, the following nomenclature is used: Original amino acid, position, original amino acid, new inserted amino acid. Accordingly the insertion of lysine after glycine at position 17 is designated "Gly17GlyLys" or "G17GK".

Parent Signal Peptides and Prepropeptides

In the present invention, the parent signal peptide or prepropeptide can be any signal peptide or prepropeptide that has at least 70% identity to amino acids 1 to 17 of SEQ ID NO: 2 or amino acids 1 to 22 of SEQ ID NO: 2; respectively; is encoded by a polynucleotide comprising or consisting of a polynucleotide comprising a nucleotide sequence that has at least 70% identity to nucleotides 1 to 51 of SEQ ID NO: 1 or nucleotides 1 to 66 of SEQ ID NO: 1, respectively, or their complementary strands; or is encoded by a polynucleotide comprising or consisting of a nucleotide sequence that hybridizes under stringency conditions with nucleotides 1 to 51 of SEQ ID NO: 1 or nucleotides 1 to 66 of SEQ ID NO: 1, respectively, or their complementary strands.

In a first aspect, the parent signal peptide or prepropeptide has a degree of identity to amino acids 1 to 17 of SEQ ID NO: 2 or amino acids 1 to 22 of SEQ ID NO: 2, respectively, of at least about 70%, preferably at least about 75%, more preferably at least about 80%, more preferably at least about 85%, even more preferably at least about 90%, most preferably at least about 95%, and even most preferably at least about 96%, 97%, 98%, or 99%, which have the ability to direct a polypeptide into a cell's secretory pathway to secrete a polypeptide with biological activity (hereinafter "homologous peptides").

In another preferred aspect, the homologous parent signal peptides, propeptides, or prepropeptides have amino acid sequences which differ by five amino acids, preferably by four amino acids, more preferably by three amino acids, even more preferably by two amino acids, and most preferably by one amino acid from amino acids 1 to 17 of SEQ ID NO: 2 or amino acids 1 to 22 of SEQ ID NO: 2; respectively. For purposes of the present invention, the degree of identity between two amino acid sequences is determined by the Clustal method (Higgins, 1989, CABIOS 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

In another preferred aspect, the parent signal peptide or prepropeptide comprises amino acids 1 to 17 of SEQ ID NO: 2 or amino acids 1 to 22 of SEQ ID NO: 2, respectively, or fragments thereof, which have the ability to direct the polypeptide into a cell's secretory pathway to secrete a polypeptide with biological activity. In a more preferred aspect, the parent signal peptide or prepropeptide comprises amino acids 1 to 17 of SEQ ID NO: 2 or amino acids 1 to 22 of SEQ ID NO: 2, respectively. In another preferred aspect, the parent signal peptide or prepropeptide consists of amino acids 1 to 17 of SEQ ID NO: 2 or amino acids 1 to 22 of SEQ ID NO: 2, respectively, or fragments thereof, which have the ability to direct a polypeptide into a cell's secretory pathway to secrete a polypeptide with biological activity. In another more preferred aspect, the parent signal peptide or prepropeptide consists of amino acids 1 to 17 of SEQ ID NO: 2 or amino acids 1 to 22 of SEQ ID NO: 2, respectively.

The present invention also encompasses polynucleotides comprising or consisting of nucleotide sequences which encode a parent signal peptide or prepropeptide having the amino acid sequence of amino acids 1 to 17 of SEQ ID NO: 2 or amino acids 1 to 22 of SEQ ID NO: 2, respectively, which differ from nucleotides 1 to 51 of SEQ ID NO: 1 or nucleotides 1 to 66 of SEQ ID NO: 1, respectively, by virtue of the degeneracy of the genetic code. The present invention also relates to subsequences of nucleotides 1 to 51 of SEQ ID NO: 1 or nucleotides 1 to 66 of SEQ ID NO: 1 which encode fragments of amino acids 1 to 17 of SEQ ID NO: 2 or amino acids 1 to 22 of SEQ ID NO: 2, respectively, which have the ability to direct a polypeptide into a cell's secretory pathway to secrete a polypeptide with biological activity.

A subsequence of nucleotides 1 to 51 of SEQ ID NO: 1 or nucleotides 1 to 66 of SEQ ID NO: 1 is a nucleic acid sequence encompassed by nucleotides 1 to 51 of SEQ ID NO: 1 or nucleotides 1 to 66 of SEQ ID NO: 1, except that one or more (several) nucleotides have been deleted from the 5' and/or 3' end. A fragment of amino acids 1 to 17 of SEQ ID NO: 2 or amino acids 1 to 22 of SEQ ID NO: 2, is a peptide having one or more (several) amino acids deleted from the amino and/or carboxy terminus of this amino acid sequence.

In a second aspect, the parent signal peptide or prepropeptide is encoded by a polynucleotide comprising a nucleotide sequence that has a degree of identity to nucleotides 1 to 51 of SEQ ID NO: 1 or nucleotides 1 to 66 of SEQ ID NO: 1, respectively, of at least about 70%, preferably at least about 75%, more preferably at least about 80%, more preferably at least about 85%, even more preferably at least about 90%, most preferably at least about 95%, and even most preferably at least about 96%, 97%, 98%, or 99%; or allelic variants and subsequences of nucleotides 1 to 51 of SEQ ID NO: 1 or nucleotides 1 to 66 of SEQ ID NO: 1, which encode fragments of a signal peptide or prepropeptide, which have the ability to direct a polypeptide into a cell's secretory pathway to secrete a polypeptide with biological activity. For purposes of the present invention, the degree of identity between two nucleic acid sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

In a third aspect, the parent signal peptide or prepropeptide is encoded by a polynucleotide comprising or consisting of a nucleotide sequence which hybridizes under stringency conditions with nucleotides 1 to 51 of SEQ ID NO: 1 or nucleotides 1 to 66 of SEQ ID NO: 1, respectively, or their complementary strands (J. Sambrook, E. F. Fritsch, and T. Maniatus, 1989, *Molecular Cloning, A Laboratory Manual,* 2d edition, Cold Spring Harbor, New York).

Nucleotides 1 to 66 of SEQ ID NO: 1 or a subsequence thereof, as well as amino acids 1 to 22 of SEQ ID NO: 2, or a fragment thereof, may be used to design a nucleic acid probe to identify and clone DNA encoding signal peptides, propeptides, or prepropeptides from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 30, and more preferably at least 45 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

Thus, a genomic DNA or cDNA library prepared from such other organisms may be screened for DNA which hybridizes with the probes described above and which encodes a signal peptide or prepropeptide. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with nucleotides 1 to 51 of SEQ ID NO: 1 or nucleotides 1 to 66 of SEQ ID NO: 1, or subsequences thereof, the carrier material is used in a Southern blot. For purposes of the present invention, hybridization indicates that the nucleic acid sequence hybridizes to a labeled nucleic acid probe corresponding to nucleotides 1 to 51 of SEQ ID NO: 1 or nucleotides 1 to 66 of SEQ ID NO: 1, or their complementary strands, or a subsequence thereof, under stringency conditions defined herein. Molecules to which the nucleic acid probe hybridizes under these conditions can be detected using, for example, X-ray film.

In a preferred aspect, the nucleic acid probe is a polynucleotide comprising a nucleotide sequence which encodes the signal peptide or prepropeptide of amino acids 1 to 17 of SEQ ID NO: 2 or amino acids 1 to 22 of SEQ ID NO: 2, respectively, or a subsequence thereof. In another preferred aspect, the nucleic acid probe is nucleotides 1 to 51 of SEQ ID NO: 1 or nucleotides 1 to 66 of SEQ ID NO: 1.

For short probes that are about 15 nucleotides to about 60 nucleotides in length, stringency conditions are defined as prehybridization, hybridization, and washing post-hybridization at 5° C. to 10° C. below the calculated $T_m$, using the calculation according to Bolton and McCarthy (1962, *Proceedings of the National Academy of Sciences USA* 48: 1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes that are about 15 nucleotides to about 60 nucleotides in length, the carrier material is washed once in 6×SCC plus 0.1% SDS for 15 minutes and twice each for 15 minutes using 6×SSC at 5° C. to 10° C. below the calculated $T_m$.

Variant Signal Peptides or Prepropeptides

Variants of a parent signal peptide or parent prepropeptide can be prepared according to site-directed mutagenesis procedures well known in the art. Site-directed mutagenesis is a technique in which one or several mutations are created at a defined site in a polynucleotide molecule encoding the parent signal peptide or parent prepropeptide. The technique can be performed in vitro or in vivo.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the a parent signal peptide or parent prepropeptide and subsequent ligation of an oligonucleotide containing the mutation in the polynucleotide. Usually the restriction enzyme that digests the plasmid and the oligonucleotide is the same, permitting sticky ends of the plasmid and insert to ligate to one another. See, for example, Scherer and Davis, 1979, *Proc. Natl. Acad. Sci. USA* 76: 4949-4955; and Barton et al., 1990, *Nucleic Acids Research* 18: 7349-4966.

Site-directed mutagenesis can be accomplished in vivo by methods known in the art. See, for example, U.S. Patent Application Publication 2004/0171154; Storici et al., 2001, *Nature Biotechnology* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants of a parent signal peptide or parent prepropeptide.

In the present invention, variants of a parent signal peptide or parent prepropeptide comprise a substitution at a position corresponding to position 2 of amino acids 1 to 17 of SEQ ID NO: 2 and/or one or more (several) deletions at positions corresponding to positions 18, 19, 20, 21, and/or 22 of amino acids 18 to 22 of SEQ ID NO: 2, wherein the variant signal peptides or variant prepropeptides when operably linked (fused) in frame to a polypeptide direct the polypeptide into a cell's secretory pathway. In a preferred aspect, the variant signal peptides or variant prepropeptides comprise amino acid sequences which have a degree of identity of at least 70%, preferably at least 75%, more preferably at least 80%, more preferably at least 85%, even more preferably at least 90%, most preferably at least 95%, and even most preferably at least 96%, 97%, 98%, or 99% to amino acids 1 to 17 of SEQ ID NO: 2 or amino acids 1 to 22 of SEQ ID NO: 2, respectively. For purposes of the present invention, the degree of identity between two amino acid sequences is determined by the Clustal method (Higgins, 1989, CABIOS 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

In a preferred aspect, the number of amino acid substitutions in the variants of the present invention comprise preferably 1 substitution. In another preferred aspect, the number of amino acid deletions in the variants of the present invention comprise preferably 1, more preferably 2, even more preferably 3, most preferably 4, and even most preferably 5 deletions. In another preferred aspect, the number of amino acid substitutions in the variants of the present invention comprise preferably 1 substitution and the number of amino acid deletions in the variants of the present invention comprise preferably 1, more preferably 2, even more preferably 3, most preferably 4, and even most preferably 5 deletions.

In a preferred aspect, a variant signal peptide comprises a substitution at a position corresponding to position 2 of amino acids 1 to 17 of SEQ ID NO: 2.

In a more preferred aspect, a variant signal peptide comprises a substitution with Ala, Arg, Asn, Asp, Cys, Gln, Glu, Gly, His, Ile, Leu, Lys, Met, Phe, Pro, Ser, Thr, Trp, Tyr, or Val at a position corresponding to position 2 of amino acids 1 to 17 of SEQ ID NO: 2.

In an even more preferred aspect, a variant signal peptide comprises Lys as a substitution at a position corresponding to position 2 of amino acids 1 to 17 of SEQ ID NO: 2.

In a most preferred aspect, a variant signal peptide comprises substitution R2K at a position corresponding to position 2 of amino acids 1 to 17 of SEQ ID NO: 2.

In an even most preferred aspect, a variant signal peptide comprises or consists of substitution R2K of amino acids 1 to 17 of SEQ ID NO: 2.

In another preferred aspect, a variant prepropeptide comprises a deletion at one or more (several) positions corresponding to positions 18, 19, 20, 21, and 22 of amino acids 1 to 22 of SEQ ID NO: 2.

In another preferred aspect, a variant prepropeptide comprises a deletion of Ala, Arg, Asn, Asp, Cys, Gln, Glu, Gly, His, Ile, Leu, Lys, Met, Phe, Pro, Ser, Thr, Trp, Tyr, or Val at one or more (several) positions corresponding to positions 18, 19, 20, 21, and 22 of amino acids 1 to 22 of SEQ ID NO: 2.

In another preferred aspect, a variant prepropeptide comprises deletions at positions corresponding to positions 18, 19, 20, 21, and 22 of amino acids 1 to 22 of SEQ ID NO: 2.

In another preferred aspect, a variant prepropeptide comprises deletions of Ala, Arg, Asn, Asp, Cys, Gln, Glu, Gly, His, Ile, Leu, Lys, Met, Phe, Pro, Ser, Thr, Trp, Tyr, or Val at positions corresponding to positions 18, 19, 20, 21, and 22 of amino acids 1 to 22 of SEQ ID NO: 2.

In another more preferred aspect, a variant prepropeptide comprises one or more (several) deletions of Ser, Pro, Ile, Arg, and Arg at positions corresponding to positions 18, 19, 20, 21, and 22, respectively, of amino acids 1 to 22 of SEQ ID NO: 2.

In another even more preferred aspect, a variant prepropeptide comprises deletions Ser, Pro, Ile, Arg, and Arg at positions corresponding to positions 18, 19, 20, 21, and 22, respectively, of amino acids 1 to 22 of SEQ ID NO: 2.

In another most preferred aspect, a variant prepropeptide comprises one or more (several) deletions of S18*, P19*, I20*, R21*, and R22* of amino acids 1 to 22 of SEQ ID NO: 2.

In another even most preferred aspect, a variant prepropeptide comprises or consists of deletions S18*, P19*, I20*, R21*, and R22* of SEQ ID NO: 2.

In another preferred aspect, a variant prepropeptide comprises a substitution at a position corresponding to position 2 of amino acids 1 to 22 of SEQ ID NO: 2.

In another more preferred aspect, a variant prepropeptide comprises a substitution with Ala, Arg, Asn, Asp, Cys, Gln, Glu, Gly, His, Ile, Leu, Lys, Met, Phe, Pro, Ser, Thr, Trp, Tyr, or Val at a position corresponding to position 2 of amino acids 1 to 22 of SEQ ID NO: 2.

In another even more preferred aspect, a variant prepropeptide comprises Lys as a substitution at a position corresponding to position 2 of amino acids 1 to 22 of SEQ ID NO: 2.

In another most preferred aspect, a variant prepropeptide comprises substitution R2K at a position corresponding to position 2 of amino acids 1 to 22 of SEQ ID NO: 2.

In another even most preferred aspect, a variant prepropeptide comprises or consists of substitution R2K of amino acids 1 to 22 of SEQ ID NO: 2.

In another preferred aspect, a variant prepropeptide comprises a substitution at a position corresponding to position 2 of amino acids 1 to 22 of SEQ ID NO: 2 and a deletion at one or more (several) positions corresponding to positions 18, 19, 20, 21, and 22 of amino acids 1 to 22 of SEQ ID NO: 2.

In another more preferred aspect, a variant prepropeptide comprises a substitution with Ala, Arg, Asn, Asp, Cys, Gln, Glu, Gly, His, Ile, Leu, Lys, Met, Phe, Pro, Ser, Thr, Trp, Tyr, or Val at a position corresponding to position 2 of amino acids 1 to 22 of SEQ ID NO: 2 and a deletion of Ala, Arg, Asn, Asp, Cys, Gln, Glu, Gly, His, Ile, Leu, Lys, Met, Phe, Pro, Ser, Thr, Trp, Tyr, or Val at one or more (several) positions corresponding to positions 18, 19, 20, 21, and 22 of amino acids 1 to 22 of SEQ ID NO: 2.

In another even more preferred aspect, a variant prepropeptide comprises a substitution at a position corresponding to position 2 of amino acids 1 to 22 of SEQ ID NO: 2 and deletions at positions corresponding to positions 18, 19, 20, 21, and 22 of amino acids 1 to 22 of SEQ ID NO: 2.

In another even more preferred aspect, a variant prepropeptide comprises a substitution with Ala, Arg, Asn, Asp, Cys, Gln, Glu, Gly, His, Ile, Leu, Lys, Met, Phe, Pro, Ser, Thr, Trp, Tyr, or Val at a position corresponding to position 2 of amino acids 1 to 22 of SEQ ID NO: 2 and deletions of Ala, Arg, Asn, Asp, Cys, Gln, Glu, Gly, His, Ile, Leu, Lys, Met, Phe, Pro, Ser, Thr, Trp, Tyr, or Val at positions corresponding to positions 18, 19, 20, 21, and 22 of amino acids 1 to 22 of SEQ ID NO: 2.

In another even more preferred aspect, a variant prepropeptide comprises Lys as a substitution at a position corresponding to position 2 of amino acids 1 to 22 of SEQ ID NO: 2 and one or more (several) deletions of Ser, Pro, Ile, Arg, and Arg at positions corresponding to positions 18, 19, 20, 21, and 22, respectively, of amino acids 1 to 22 of SEQ ID NO: 2.

In another even more preferred aspect, a variant prepropeptide comprises substitution Lys at a position corresponding to position 2 of amino acids 1 to 22 of SEQ ID NO: 2 and deletions of Ser, Pro, Ile, Arg, and Arg at positions corresponding to positions 18, 19, 20, 21, and 22, respectively, of amino acids 1 to 22 of SEQ ID NO: 2.

In another even more preferred aspect, a variant prepropeptide comprises substitution R2K at a position corresponding to position 2 of amino acids 1 to 22 of SEQ ID NO: 2 and deletions S18*, P19*, I20*, R21*, and R22* at positions corresponding to positions 18, 19, 20, 21, and 22, respectively, of amino acids 1 to 22 of SEQ ID NO: 2.

In another most preferred aspect, a variant prepropeptide comprises or consists of substitution R2K of amino acids 1 to 22 of SEQ ID NO: 2 and one or more (several) deletions of S18*, P19*, I20*, R21*, and R22* of amino acids 1 to 22 of SEQ ID NO: 2.

In another even most preferred aspect, a variant prepropeptide comprises or consists of substitution R2K of amino acids 1 to 22 of SEQ ID NO: 2 and deletions S18*, P19*, I20*, R21*, and R22* of amino acids 1 to 22 of SEQ ID NO: 2.

In another even most preferred aspect, the variant signal peptide is SEQ ID NO: 4. In another even most preferred aspect, the variant signal peptide coding sequence is SEQ ID NO: 3. In another even most preferred aspect, the variant prepropeptide is SEQ ID NO: 6. In another even most preferred aspect, the variant prepropeptide coding sequence is SEQ ID NO: 5.

The variants of the present invention may further comprise one or more (several) additional substitutions, deletions, and/or insertions of the amino acid sequence.

Polynucleotides

The present invention also relates to isolated polynucleotides that encode variant signal peptides and variant prepropeptides of a parent signal peptide and parent prepropeptide, respectively, wherein the variant signal peptides and variant prepropeptides comprise a substitution at a position corresponding to position 2 of amino acids 1 to 17 of SEQ ID NO: 2 and/or one or more (several) deletions at positions corresponding to positions 18, 19, 20, 21, and/or 22 of amino acids 18 to 22 of SEQ ID NO: 2, wherein the variant signal peptides or variant prepropeptides when operably linked (fused) in frame to a polypeptide direct the polypeptide into a cell's secretory pathway.

The parent signal peptide or prepropeptide can be any signal peptide or prepropeptide that has at least 70% identity to amino acids 1 to 17 of SEQ ID NO: 2 or amino acids 1 to 22 of SEQ ID NO: 2; respectively; is encoded by a polynucleotide comprising or consisting of a nucleotide sequence that has at least 70% identity to nucleotides 1 to 51 of SEQ ID NO: 1 or nucleotides 1 to 66 of SEQ ID NO: 1, respectively, or their complementary strands; or is encoded by a polynucleotide comprising or consisting of a nucleotide sequence that hybridizes under stringency conditions with nucleotides 1 to 51 of SEQ ID NO: 1 or nucleotides 1 to 66 of SEQ ID NO: 1, respectively, or their complementary strands, as described herein.

In a preferred aspect, the isolated polynucleotides encode variant signal peptides or variant prepropeptides comprising amino acid sequences which have a degree of identity of at least 70%, preferably at least 75%, more preferably at least 80%, more preferably at least 85%, even more preferably at least 90%, most preferably at least 95%, and even most preferably at least 96%, 97%, 98%, or 99% to amino acids 1 to 17 of SEQ ID NO: 2 or amino acids 1 to 22 of SEQ ID NO: 2, respectively.

In a preferred aspect, an isolated polynucleotide encodes a variant signal peptide comprising a substitution at a position corresponding to position 2 of amino acids 1 to 17 of SEQ ID NO: 2.

In a more preferred aspect, an isolated polynucleotide encodes a variant signal peptide comprising a substitution with Ala, Arg, Asn, Asp, Cys, Gln, Glu, Gly, His, Ile, Leu, Lys, Met, Phe, Pro, Ser, Thr, Trp, Tyr, or Val at a position corresponding to position 2 of amino acids 1 to 17 of SEQ ID NO: 2.

In an even more preferred aspect, an isolated polynucleotide encodes a variant signal peptide comprising Lys as a substitution at a position corresponding to position 2 of amino acids 1 to 17 of SEQ ID NO: 2.

In a most preferred aspect, an isolated polynucleotide encodes a variant signal peptide comprising substitution R2K at a position corresponding to position 2 of amino acids 1 to 17 of SEQ ID NO: 2.

In an even most preferred aspect, an isolated polynucleotide encodes a variant signal peptide comprising or consisting of substitution R2K of amino acids 1 to 17 of SEQ ID NO: 2.

In another preferred aspect, a variant prepropeptide comprising a deletion at one or more (several) positions corresponding to positions 18, 19, 20, 21, and 22 of amino acids 1 to 22 of SEQ ID NO: 2.

In another preferred aspect, an isolated polynucleotide encodes a variant prepropeptide comprising a deletion of Ala, Arg, Asn, Asp, Cys, Gln, Glu, Gly, His, Ile, Leu, Lys, Met, Phe, Pro, Ser, Thr, Trp, Tyr, or Val at one or more (several) positions corresponding to positions 18, 19, 20, 21, and 22 of amino acids 1 to 22 of SEQ ID NO: 2.

In another preferred aspect, an isolated polynucleotide encodes a variant prepropeptide comprising deletions at positions corresponding to positions 18, 19, 20, 21, and 22 of amino acids 1 to 22 of SEQ ID NO: 2.

In another preferred aspect, an isolated polynucleotide encodes a variant prepropeptide comprising deletions of Ala, Arg, Asn, Asp, Cys, Gln, Glu, Gly, His, Ile, Leu, Lys, Met, Phe, Pro, Ser, Thr, Trp, Tyr, or Val at positions corresponding to positions 18, 19, 20, 21, and 22 of amino acids 1 to 22 of SEQ ID NO: 2.

In another more preferred aspect, an isolated polynucleotide encodes a variant prepropeptide comprising one or more (several) deletions of Ser, Pro, Ile, Arg, and Arg at positions corresponding to positions 18, 19, 20, 21, and 22, respectively, of amino acids 1 to 22 of SEQ ID NO: 2.

In another even more preferred aspect, an isolated polynucleotide encodes a variant prepropeptide comprising deletions Ser, Pro, Ile, Arg, and Arg at positions corresponding to positions 18, 19, 20, 21, and 22, respectively, of amino acids 1 to 22 of SEQ ID NO: 2.

In another most preferred aspect, an isolated polynucleotide encodes a variant prepropeptide comprising one or more (several) deletions of S18*, P19*, I20*, R21*, and R22* of amino acids 1 to 22 of SEQ ID NO: 2.

In another even most preferred aspect, an isolated polynucleotide encodes a variant prepropeptide comprising or consisting of deletions S18*, P19*, I20*, R21*, and R22* of amino acids 1 to 22 of SEQ ID NO: 2.

In another preferred aspect, an isolated polynucleotide encodes a variant prepropeptide comprising a substitution at a position corresponding to position 2 of amino acids 1 to 22 of SEQ ID NO: 2.

In another more preferred aspect, an isolated polynucleotide encodes a variant prepropeptide comprising a substitution with Ala, Arg, Asn, Asp, Cys, Gln, Glu, Gly, His, Ile, Leu, Lys, Met, Phe, Pro, Ser, Thr, Trp, Tyr, or Val at a position corresponding to position 2 of amino acids 1 to 22 of SEQ ID NO: 2.

In another even more preferred aspect, an isolated polynucleotide encodes a variant prepropeptide comprising Lys as a substitution at a position corresponding to position 2 of amino acids 1 to 22 of SEQ ID NO: 2.

In another most preferred aspect, an isolated polynucleotide encodes a variant prepropeptide comprising substitution R2K at a position corresponding to position 2 of amino acids 1 to 22 of SEQ ID NO: 2.

In another even most preferred aspect, an isolated polynucleotide encodes a variant prepropeptide comprising or consisting of substitution R2K of amino acids 1 to 22 of SEQ ID NO: 2.

In another preferred aspect, an isolated polynucleotide encodes a variant prepropeptide comprising a substitution at a position corresponding to position 2 of amino acids 1 to 22 of SEQ ID NO: 2 and a deletion at one or more (several) positions corresponding to positions 18, 19, 20, 21, and 22 of amino acids 1 to 22 of SEQ ID NO: 2.

In another more preferred aspect, an isolated polynucleotide encodes a variant prepropeptide comprising a substitution with Ala, Arg, Asn, Asp, Cys, Gln, Glu, Gly, His, Ile, Leu, Lys, Met, Phe, Pro, Ser, Thr, Trp, Tyr, or Val at a position corresponding to position 2 of amino acids 1 to 22 of SEQ ID NO: 2 and a deletion of Ala, Arg, Asn, Asp, Cys, Gln, Glu, Gly, His, Ile, Leu, Lys, Met, Phe, Pro, Ser, Thr, Trp, Tyr, or Val at one or more (several) positions corresponding to positions 18, 19, 20, 21, and 22 of amino acids 1 to 22 of SEQ ID NO: 2.

In another even more preferred aspect, an isolated polynucleotide encodes a variant prepropeptide comprising a substitution at a position corresponding to position 2 of amino acids 1 to 22 of SEQ ID NO: 2 and deletions at positions corresponding to positions 18, 19, 20, 21, and 22 of amino acids 1 to 22 of SEQ ID NO: 2.

In another even more preferred aspect, an isolated polynucleotide encodes a variant prepropeptide comprising a substitution with Ala, Arg, Asn, Asp, Cys, Gln, Glu, Gly, His, Ile, Leu, Lys, Met, Phe, Pro, Ser, Thr, Trp, Tyr, or Val at a position corresponding to position 2 of amino acids 1 to 22 of SEQ ID NO: 2 and deletions of Ala, Arg, Asn, Asp, Cys, Gln, Glu, Gly, His, Ile, Leu, Lys, Met, Phe, Pro, Ser, Thr, Trp, Tyr, or Val at positions corresponding to positions 18, 19, 20, 21, and 22 of amino acids 1 to 22 of SEQ ID NO: 2.

In another even more preferred aspect, an isolated polynucleotide encodes a variant prepropeptide comprising Lys as a substitution at a position corresponding to position 2 of amino acids 1 to 22 of SEQ ID NO: 2 and one or more (several) deletions of Ser, Pro, Ile, Arg, and Arg at positions corresponding to positions 18, 19, 20, 21, and 22, respectively, of amino acids 1 to 22 of SEQ ID NO: 2.

In another even more preferred aspect, an isolated polynucleotide encodes a variant prepropeptide comprising substitution R2K at a position corresponding to position 2 of amino acids 1 to 22 of SEQ ID NO: 2 and one or more (several) deletions of S18*, P19*, I20*, R21*, and R22* at positions corresponding to positions 18, 19, 20, 21, and 22, respectively, of amino acids 1 to 22 of SEQ ID NO: 2.

In another even more preferred aspect, an isolated polynucleotide encodes a variant prepropeptide comprising substitution R2K at a position corresponding to position 2 of amino acids 1 to 22 of SEQ ID NO: 2 and deletions S18*, P19*, I20*, R21*, and R22* at positions corresponding to positions 18, 19, 20, 21, and 22, respectively, of amino acids 1 to 22 of SEQ ID NO: 2.

In another most preferred aspect, an isolated polynucleotide encodes a variant prepropeptide comprising or consisting of substitution R2K of amino acids 1 to 22 of SEQ ID NO: 2 and one or more (several) deletions of S18*, P19*, I20*, R21*, and R22* of amino acids 1 to 22 of SEQ ID NO: 2.

In another even most preferred aspect, an isolated polynucleotide encodes a variant prepropeptide comprising or consisting of substitution R2K of amino acids 1 to 22 of SEQ ID NO: 2 and deletions S18*, P19*, I20*, R21*, and R22* of amino acids 1 to 22 of SEQ ID NO: 2.

In another even most preferred aspect, an isolated polynucleotide encodes the variant signal peptide of SEQ ID NO: 4. In another even most preferred aspect, an isolated polynucleotide encoding the variant signal peptide of SEQ ID NO: 4 is SEQ ID NO: 3. In another even most preferred aspect, an isolated polynucleotide encodes the variant prepropeptide of SEQ ID NO: 6. In another even most preferred aspect, an isolated polynucleotide encoding the variant prepropeptide of SEQ ID NO: 6 is SEQ ID NO: 5.

The term "isolated polynucleotide" as used herein refers to a polynucleotide which is essentially free of other polynucleotides, e.g., at least 20% pure, preferably at least 40% pure, more preferably at least 60% pure, even more preferably at least 80% pure, and most preferably at least 90% pure as determined by agarose electrophoresis.

The present invention also relates to methods for obtaining a polynucleotide encoding a variant signal peptide or variant prepropeptide, comprising: (a) introducing into a parent signal peptide coding sequence or a parent prepropeptide coding sequence a substitution at a position corresponding to position 2 of amino acids 1 to 22 of SEQ ID NO: 2 and/or a deletion at one or more (several) positions corresponding to positions 18, 19, 20, 21, and/or 22 of amino acids 1 to 22 of SEQ ID NO: 2, wherein the variant signal peptide or variant prepropeptide when operably linked in frame to a polypeptide having biological activity directs the polypeptide into a cell's secretory pathway; and (b) recovering the polynucleotide.

Polypeptides

The polypeptide may be native or heterologous (foreign) to the fungal host cell of interest. The term "heterologous polypeptide" is defined herein as a polypeptide which is not native to the host cell; or a native polypeptide in which structural modifications have been made to alter the native polypeptide.

The polypeptide may be any polypeptide having a biological activity of interest. The term "polypeptide" is not meant herein to refer to a specific length of the encoded product and, therefore, encompasses peptides, oligopeptides, and proteins. The term "polypeptide" also encompasses hybrid polypeptides, which comprise a combination of partial or complete polypeptide sequences obtained from at least two different polypeptides wherein one or more (several) may be heterologous to the fungal cell. Polypeptides further include naturally occurring allelic and engineered variations of a polypeptide.

In a preferred aspect, the polypeptide is an antibody, antigen, antimicrobial peptide, enzyme, growth factor, hormone, immunodilator, neurotransmitter, receptor, reporter protein, structural protein, and transcription factor.

In a more preferred aspect, the polypeptide is an oxidoreductase, transferase, hydrolase, lyase, isomerase, or ligase. In a most preferred aspect, the polypeptide is an alpha-glucosidase, aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, glucocerebrosidase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, urokinase, or xylanase.

In another preferred aspect, the polypeptide is an albumin, collagen, tropoelastin, elastin, or gelatin.

In a preferred aspect, the polypeptide is a lipase. In a more preferred aspect, the polypeptide is a lipase obtained from *Thermomyces*. In an even more preferred aspect, the polypeptide is a wild-type lipase obtained from *Thermomyces lanuginosus*. In a most preferred aspect, the polypeptide is a wild-type *Thermomyces lanuginosus* lipase comprising or consisting of the mature polypeptide of SEQ ID NO: 8. In an even most preferred aspect, the mature polypeptide of SEQ ID NO: 8 is encoded by the mature polypeptide coding sequence of SEQ ID NO: 7. In another even more preferred aspect, the polypeptide is a variant lipase obtained from a *Thermomyces lanuginosus* lipase. In another most preferred aspect, the polypeptide is a *Thermomyces lanuginosus* variant lipase comprising or consisting of the mature polypeptide of SEQ ID NO: 10. In another even most preferred aspect, the mature polypeptide of SEQ ID NO: 10 is encoded by the mature polypeptide coding sequence of SEQ ID NO: 9.

In a preferred aspect, the mature polypeptide is amino acids 23 to 291 of SEQ ID NO: 8. In another preferred aspect, the mature polypeptide coding sequence is nucleotides 67 to 918 of SEQ ID NO: 7. In another preferred aspect, the mature polypeptide is amino acids 23 to 291 of SEQ ID NO: 10. In another preferred aspect, the mature polypeptide coding sequence is nucleotides 67 to 873 of SEQ ID NO: 9.

A polynucleotide encoding a polypeptide may be obtained from any prokaryotic, eukaryotic, or other source. For purposes of the present invention, the term "obtained from" as used herein in connection with a given source shall mean that the polypeptide is produced by the source or by a cell in which a gene from the source has been inserted.

The techniques used to isolate or clone a nucleic acid sequence encoding a polypeptide are known in the art and include isolation from genomic DNA, preparation from cDNA, or a combination thereof. The cloning of the nucleic acid sequence from such genomic DNA can be effected, e.g., by using the well known polymerase chain reaction (PCR). See, for example, Innis et al., 1990, *PCR Protocols: A Guide to Methods and Application*, Academic Press, New York. The cloning procedures may involve excision and isolation of a desired nucleic acid fragment comprising the nucleic acid sequence encoding the polypeptide, insertion of the fragment into a vector molecule, and incorporation of the recombinant vector into the mutant fungal cell where multiple copies or clones of the nucleic acid sequence will be replicated. The nucleic acid sequence may be of genomic, cDNA, RNA, semisynthetic, synthetic origin, or any combinations thereof.

Nucleic Acid Constructs

The present invention also relates to nucleic acid constructs comprising a polynucleotide encoding a polypeptide operably linked to a variant signal peptide coding sequence or variant prepropeptide coding sequence of the present invention and one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleotide molecule, either single- or double-stranded, which is isolated from a naturally occurring gene or which has been modified to contain segments of nucleic acids combined and juxtaposed in a manner that would not otherwise exist in nature. The term nucleic acid construct is synonymous with the term expression cassette when the nucleic acid construct contains a coding sequence and all the control sequences required for expression of the coding sequence.

An isolated polynucleotide encoding a polypeptide may be further manipulated in a variety of ways to provide for expression of the polypeptide. Manipulation of the nucleotide sequence of the polynucleotide prior to its insertion into a vector may be desirable or necessary depending on the expression vector. The techniques for modifying nucleotide sequences utilizing recombinant DNA methods are well known in the art.

In the methods of the present invention, the polynucleotide may comprise one or more native control sequences or one or more of the native control sequences may be replaced with one or more control sequences foreign to the polynucleotide for improving expression of the coding sequence in a host cell.

The term "control sequences" is defined herein to include all components which are necessary or advantageous for the expression of a polypeptide of interest. Each control sequence may be native or foreign to the polynucleotide encoding the polypeptide. Such control sequences include, but are not limited to, a leader, polyadenylation sequence, propeptide sequence, variant signal peptide coding sequence or variant prepropeptide coding sequence of the present invention, and transcription terminator. At a minimum, the control sequences include a variant signal peptide coding sequence or variant prepropeptide coding sequence of the present invention, and transcriptional and translational stop signals. The control sequences may be provided with linkers for the purpose of introducing specific restriction sites facilitating ligation of the control sequences with the coding region of the polynucleotide sequence encoding a polypeptide.

The control sequence may be an appropriate promoter sequence, which is recognized by a host cell for expression of a polynucleotide. The promoter sequence contains transcriptional control sequences which mediate the expression of the polypeptide. The promoter may be any sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Sac-* charomyces cerevisiae 3-phosphoglycerate kinase. Other useful promoters for yeast host cells are described by Romanos et al., 1992, *Yeast* 8: 423-488.

The control sequence may be a suitable transcription terminator sequence, which is recognized by a host cell to terminate transcription. The terminator sequence is operably linked to the 3' terminus of the polynucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the polynucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, which is operably linked to the 3' terminus of the polynucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Saccharomyces cerevisiae* alpha-factor, *Rhizomucor miehei* aspartic proteinase, *Thermomyces lanuginosus* lipase, and *Myceliophthora thermophila* laccase (WO 95/33836).

Where both signal peptide and propeptide regions are present at the amino terminus of a polypeptide, the propeptide region is linked in frame to the amino terminus of a polypeptide and the signal peptide region is linked in frame to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the polynucleotide comprising a nucleotide sequence encoding the polypeptide would be operably linked with the regulatory sequence.

Expression Vectors

The present invention also relates to recombinant expression vectors comprising a variant signal peptide coding sequence or variant prepropeptide coding sequence of the present invention, a polynucleotide sequence encoding a polypeptide of interest, and transcriptional and translational stop signals. The various nucleotide and control sequences described above may be joined together to produce a recombinant expression vector which may include one or more convenient restriction sites to allow for insertion or substitution of the promoter and/or polynucleotide sequence encoding the polypeptide at such sites. Alternatively, the polynucleotide sequence may be expressed by inserting the polynucleotide sequence or a nucleic acid construct comprising the variant signal peptide coding sequence or variant prepropeptide coding sequence and polynucleotide sequence encoding the polypeptide into an appropriate vector for expression. In creating the expression vector, the coding sequence is located in the vector so that the coding sequence is operably linked to a variant signal peptide coding sequence or variant prepropeptide coding sequence of the present invention and one or more appropriate control sequences for expression.

The recombinant expression vector may be any vector (e.g., a plasmid or virus) which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain an element(s) that permits stable integration of the vector into the host cell's genome or autonomous replication of the vector in the cell independent of the genome.

For integration into the host cell genome, the vector may rely on the polynucleotide sequence encoding the polypeptide or any other element of the vector for stable integration of the vector into the genome by homologous or nonhomologous recombination. Alternatively, the vector may contain additional nucleotide sequences for directing integration by homologous recombination into the genome of the host cell. The additional nucleotide sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

Examples of origins of replication useful in a filamentous fungal cell are AMA1 and ANSI (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide encoding a polypeptide may be inserted into the host cell to increase production of the gene product. An increase in the copy number of the polynucleotide can be obtained by integrating at least one additional copy of the nucleotide sequence into the host cell genome or by including an amplifiable selectable marker gene with the nucleotide sequence where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a variant signal peptide coding sequence or variant prepropeptide coding sequence of the present invention operably linked to a polynucleotide encoding a polypeptide, which are advantageously used in the recombinant production of the polypeptide. A vector comprising a variant signal peptide coding sequence or variant prepropeptide coding sequence of the present invention operably linked to a polynucleotide encoding a polypeptide is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any fungal cell useful in the methods of the present invention. "Fungi" as used herein includes the phyla Ascomycota, Basidiomycota, Chytridiomycota, and Zygomycota (as defined by Hawksworth et al., *In, Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, *Soc. App. Bacteriol. Symposium Series* No. 9, 1980).

In a more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In an even most preferred aspect, the yeast host cell is *Saccharomyces cerevisiae* JG169 (MAT-α, ura3-52, leu2-3, pep4-1137, his3Δ2, prb1::leu2, Δpre1::his3) (U.S. Pat. No. 5,770,406).

In another preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a more preferred aspect, the filamentous fungal host cell is a cell of a species of, but not limited to, *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma*.

In an even more preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable procedures for transformation of *Trichoderma reesei* host cells is described in Penttila et al., 1987, *Gene* 61: 155-164, and Gruber et al., 1990, *Curr Genet.* 18(1):71-6. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

The present invention is further described by the following examples which should not be construed as limiting the scope of the invention.

EXAMPLES

Chemicals used as buffers and substrates were commercial products of at least reagent grade.

DNA Sequencing

DNA sequencing was performed using an Applied Biosystems Model 3130X Genetic Analyzer (Applied Biosystems, Foster City, Calif., USA) using dye terminator chemistry (Giesecke et al., 1992, *Journal of Virol. Methods* 38: 47-60). Sequences were assembled using phred/phrap/consed (University of Washington, Seattle, Wash., USA) with sequence specific primers.

Strains

*Saccharomyces cerevisiae* JG169 (MAT-α, ura3-52, leu2-3, pep4-1137, his3Δ2, prb1::leu2, Δpre1::his3) (U.S. Pat. No. 5,770,406) and *Aspergillus oryzae* BECh2 (Δa1p, Δamy, CPA-, KA-, Δnp1) (WO 00/39322) were used as host strains in the Examples herein.

Media and Solutions

YPD medium was composed per liter of 10 g of yeast extract, 20 g of Bacto peptone, and 2% glucose.

CUP minus ura medium (pH 7.0) ("original" medium) was composed per liter of 1 ml of 100 mM $CuSO_4.5H_2O$, 1.7 g of yeast nitrogen base (YNB) without amino acids and ammonium sulfate (BIO101, Carlsbad, Calif., USA), 0.8 g of CSM-ura with 40 mg of adenine (BIO101, Carlsbad, Calif., USA), 5 g of Casamino acids (Becton, Dickenson and Company, Sparks, Md., USA), 100 ml of 50% glucose, 50 ml of 0.5 M $K_2HPO_4$, and 1 ml of 100 mg/ml ampicillin.

Yeast ura minus selection medium was composed per liter of 6.7 g of yeast nitrogen base (YNB) with ammonium sulfate, 5 g of Casamino acids, 100 ml of 0.5 M succinic acid pH 5, 40 ml of 50% glucose, and 2 ml of 10 mg/ml chloramphenicol.

Yeast ura minus selection plates were composed of yeast ura minus selection medium supplemented with 20 g of Noble agar per liter.

MY25 medium was composed per liter of 25 g of maltodextrin, 2 g of $MgSO_4.7H_2O$, 10 g of $KH_2PO_4$, 2 g of citric acid, 2 g of $K_2SO_4$, 2 g of urea, 10 g of yeast extract, and 1.5 ml of AMG trace metals solution, adjusted to pH 6.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, and 3 g of citric acid.

SC ura minus medium was composed per liter of 7.5 g of yeast nitrogen base without amino acids (Fluka, Buchs, Switzerland), 11.3 g of succinic acid, 6.8 g of sodium hydroxide, 5.6 g of Casamino acids, and 0.1 g of L-tryptophan, and 100 ml of a sterile solution of 50% fructose and 400 μl of a sterile solution of 250 mg/ml of ampicillin, both added after autoclaving.

SC ura minus plates were composed of SC ura minus medium, except 100 ml of sterile 20% fructose is used, and 20 g of agar (Sigma Chemical Co., St. Louis, Mo., USA).

Synthetic Defined Medium with Uracil and Ampicillin (SDMUA) medium was composed per liter of 1.7 g yeast nitrogen base without amino acids, 5.0 g of Casamino acids, 0.8 g of CMS-Ura with 40 mg/l ADE (MP Biomedicals, Irvine, Calif., USA), 10 ml of 10 mM $CuSO_4.5H_2O$, and 10 ml of 1 M $K_2HPO_4$, and 100 ml of sterile 50% fructose and 400 μl of sterile 250 mg/ml of ampicillin, both added after autoclaving.

SOC medium was composed of 2% tryptone, 0.5% yeast extract, 10 mM NaCl, 2.5 mM KCl, 10 mM $MgCl_2$, and 10 mM $MgSO_4$, sterilized by autoclaving and then filter-sterilized glucose was added to 20 mM.

2×YT plates were composed per liter of 16 g of tryptone, 10 g of yeast extract, 5 g of NaCl, and 15 g of bacto agar.

COVE plates were composed per liter of 342 g of sucrose, 10 ml of COVE salts solution, 10 ml of 1 M acetamide, 10 ml of 1.5 M CsCl, and 25 g of Noble agar.

COVE salts solution was composed per liter of 26 g of KCl, 26 g of $MgSO_4$, 76 g of $KH_2PO_4$, and 50 ml of COVE trace metals solution.

COVE trace metals solution was composed per liter of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.H_2O$, and 10 g of $ZnSO_4.7H_2O$.

$VNO_3RLMT$ agar was composed per liter of 20 ml of 50× Vogels with 25 mM $NaNO_3$, 273.33 g of sucrose, and 15 g of low melting point agarose.

50× Vogels with 25 mM $NaNO_3$ was composed per liter of 125 g of sodium citrate dihydrate, 250 g of $KH_2PO_4$, 106.25 g of $NaNO_3$, 10 g of $MgSO_4.7H_2O$, 5 g of $CaCl_2.2H_2O$, 2.5 ml of biotin solution, and 5 ml of Vogels trace elements solution.

Biotin solution was composed of 5 mg of biotin in 100 ml of 50% ethanol.

Vogels trace elements solution was composed of 5 g of citric acid monohydrate, 5 g of $ZnSO_4.7H_2O$, 1 g of $Fe(NH_4)_2(SO_4)_2.6H_2O$, 0.25 g of $CuSO_4.5H_2O$, 0.05 g of $MnSO_4.H_2O$, 0.05 g of $H_3BO_3$, and 0.05 g of $Na_2MoO_4.2H_2O$.

Example 1

PCR Amplification of a Copper-Inducible Promoter (CUP1 Promoter)

PCR primers 997247 and 997248, shown below, were designed to amplify the *Saccharomyces cerevisiae* copper-inducible promoter (CUP1 promoter) from plasmid pCu426 (Labbe and Thiele, 1999, *Methods in Enzymology* 306: 145-153). Restriction enzyme sites, Age I and Eco RI, were incorporated into the primer design for cloning into the *Saccharomyces cerevisiae* expression plasmid pMB1537 (see Example 2).

```
Primer 997247:
                                       (SEQ ID NO: 11)
5'-CACCGGTGCATGCCTGCAGGAGCTCCTAGTTAGAAA-3'
   Age I Primer 997248:
                                       (SEQ ID NO: 12)
5'-AACTATTCTTGAATGGAATTCTAGTCGATGACTTCT-3'
                   Eco RI
```

The CUP promoter fragment was amplified by PCR using an EXPAND® High Fidelity PCR System (Roche, Indianapolis, Ind., USA). The PCR amplification reaction mixture contained approximately 50 ng of pCu426 plasmid DNA, 1 µl of primer 997247 (50 pmol/µl), 1 µl of primer 997248 (50 pmol/µl), 5 µl of 10×PCR buffer (Roche, Indianapolis, Ind., USA) with 15 mM $MgCl_2$, 1 µl of dNTP mix (10 mM each), 40.25 µl of water, and 0.75 µl (3.5 U/µl) of DNA polymerase mix (Roche, Indianapolis, Ind., USA). An EPPENDORF® MASTERCYCLER® 5333 (Eppendorf, Westbury, N.Y., USA) was used to amplify the fragment programmed for 1 cycle at 94° C. for 2 minutes; 10 cycles each at 94° C. for 15 seconds, 55° C. for 30 seconds, and 72° C. for 15 seconds; 15 cycles each at 94° C. for 15 seconds, 55° C. for 30 seconds, and 72° C. for 15 seconds plus a 5 second elongation at each successive cycle; 1 cycle at 72° C. for 7 minutes; and a 10° C. hold.

A PCR product of 246 bp was purified by 1.5% agarose gel electrophoresis using TAE buffer (4.84 g of Tris Base, 1.14 ml of glacial acetic acid, and 2 ml of 0.5 M EDTA pH 8.0 per liter) and further purified using a QIAQUICK® Gel Extraction Kit (QIAGEN Inc., Valencia, Calif., USA). The 246 bp PCR product was ligated with pCR2.1-TOPO® (Invitrogen Corporation, Carlsbad, Calif., USA) according to the manufacturer's instructions. After the incubation, 2 µl of the mixture was used to transform ONE SHOT® TOP10 chemically competent *E. coli* cells (Invitrogen Corporation, Carlsbad, Calif., USA). A 2 µl volume of the ligation mixture was added to the *E. coli* cells and incubated on ice for 5 minutes. Subsequently, the cells were heat shocked for 30 seconds at 42° C., and then placed on ice for 2 minutes. A 250 µl volume of SOC medium was added to the cells and the mixture was incubated for 1 hour at 37° C. and 250 rpm. After the incubation the colonies were spread on 2×YT plates supplemented with 100 µg of ampicillin per ml and incubated at 37° C. overnight for selection of the plasmid. Eight colonies that grew on the plates were picked with sterile toothpicks and grown overnight at 37° C., 250 rpm in a 15 ml FALCON® tube containing 3 ml of LB medium supplemented with 100 µg of ampicillin per ml. The plasmids were isolated using a BioRobot 9600 (QIAGEN Inc., Valencia, Calif., USA).

Four µl volumes of the resulting plasmid minipreps were digested with Eco RI. The digestion reactions were analyzed by agarose gel chromatography and UV analysis as previously described for the PCR reaction. Isolated plasmids containing an insert were sequenced using 1 µl of plasmid template, 1.6 ng of M13 primer (forward or reverse) (MWG Biotech, High Point, N.C., USA), and water to 6 µl. The resulting plasmid with the correct sequence was designated pBM128a (FIG. 1).

Example 2

Construction of Expression Vector pMB1537

Expression vector pMB1537 contains the yeast TPI promoter driving expression of a wild-type gene encoding a *Thermomyces lanuginosus* lipase (SEQ ID NO: 7 is the DNA sequence and SEQ ID NO: 8 is the deduced amino acid sequence; U.S. Pat. No. 5,869,438), the CYC1 terminator, and the URA3 gene as a selectable marker.

Yeast expression plasmid pSTED226 (WO 05/045018) was PCR amplified using an EXPAND® Long Template PCR System (Roche, Germany) with pSTED226 as template and the following two primers.

```
Primer 319137:
                                       (SEQ ID NO: 13)
5'-TCTAGAGGGCCGCATCATGTAATTAG-3'

Primer 19138:
                                       (SEQ ID NO: 14)
5'-GACGCCATGGTG AAGCTTTCTTTTAATCGT-3'
```

The PCR amplification reaction mixture contained approximately 50 ng of pSTED226 plasmid DNA, 1 µl of primer 319137 (50 pmol/µl), 1 µl of primer 19138 (50 pmol/µl), 5 µl of 10×PCR buffer (Roche, Indianapolis, Ind., USA) with 15 mM $MgCl_2$, 1 µl of dNTP mix (10 mM each), 40.25 µl of water, and 0.75 µl (3.5 U/µl) of DNA polymerase mix (Roche, Indianapolis, Ind., USA). A PTC Peltier Thermal Cycler (Bio-Rad Laboratories, Hercules, Calif., USA) was used to amplify the fragment programmed for 1 cycle at 94° C. for 2 minutes; 10 cycles each at 94° C. for 15 seconds, 55°

C. for 30 seconds, and 72° C. for 15 seconds; 15 cycles each at 94° C. for 15 seconds, 55° C. for 30 seconds, and 72° C. for 15 seconds plus a 5 second elongation at each successive cycle; 1 cycle at 72° C. for 7 minutes; and a 10° C. hold. After termination of the PCR procedure a PCR fragment of 5826 bp was purified and eluted with a GFX® PCR DNA and Gel Band Purification Kit according to the manufacturer's instructions (Amersham Biosciences, United Kingdom).

A gene fragment containing the *Thermomyces lanuginosus* wild-type lipase gene was PCR amplified using an EXPAND® High Fidelity PCR System with pENI1298 (WO 00/24883) as template and the following two primers:

```
Primer 349699:
                                        (SEQ ID NO: 15)
5'-CAAGAAGATTACAAACTATCAATTTCATACACAATATAAACGATTAA
AAGAAAGCTTCACCATGAGGAGCTCCCTTGTGCTGTTCTTTGTCT
CTG-3'

Primer 353031:
                                        (SEQ ID NO: 16)
5'-GAGGGCGTGAATGTAAGCGTGACATAACTAATTACATGATGCGGCCC
TCTAGATTATCAAAGACATGTCCCAATTAACCCGAAGTAC-3'
```

The PCR amplification reaction mixture contained approximately 50 ng of pENI1298 plasmid DNA, 1 µl of primer 349699 (50 pmol/µl), 1 µl of primer 353031 (50 pmol/µl), 5 µl of 10×PCR buffer (Roche, Indianapolis, Ind., USA) with 15 mM $MgCl_2$, 1 µl of dNTP mix (10 mM each), 40.25 µl of water, and 0.75 µl (3.5 U/µl) of DNA polymerase mix (Roche, Indianapolis, Ind., USA). A PTC Peltier Thermal Cycler was used to amplify the fragment programmed for 1 cycle at 94° C. for 2 minutes; 10 cycles each at 94° C. for 15 seconds, 55° C. for 30 seconds, and 72° C. for 15 seconds; 15 cycles each at 94° C. for 15 seconds, 55° C. for 30 seconds, and 72° C. for 15 seconds plus a 5 second elongation at each successive cycle; 1 cycle at 72° C. for 7 minutes; and a 10° C. hold. After termination of the PCR procedure a PCR fragment of 927 bp was purified and eluted with a GFX® PCR DNA and Gel Band Purification Kit according to the manufacturer's instructions.

The resulting two fragments, 5826 bp and 927 bp were transformed into *Saccharomyces cerevisiae* JG169 by electroporation using a GENE PULSER® and Pulse Controller (Bio-Rad, Hercules, Calif., USA) at 1.5 kvolts with a 2 mm gap cuvette according to the manufacturer's procedure. Transformation reactions contained 100 ng of PCR amplified vector DNA mixed with 100 ng of the PCR product containing the lipase gene. Transformation reactions were plated onto yeast ura minus selection plates and incubated for 5 days at 30° C.

Figure 2:
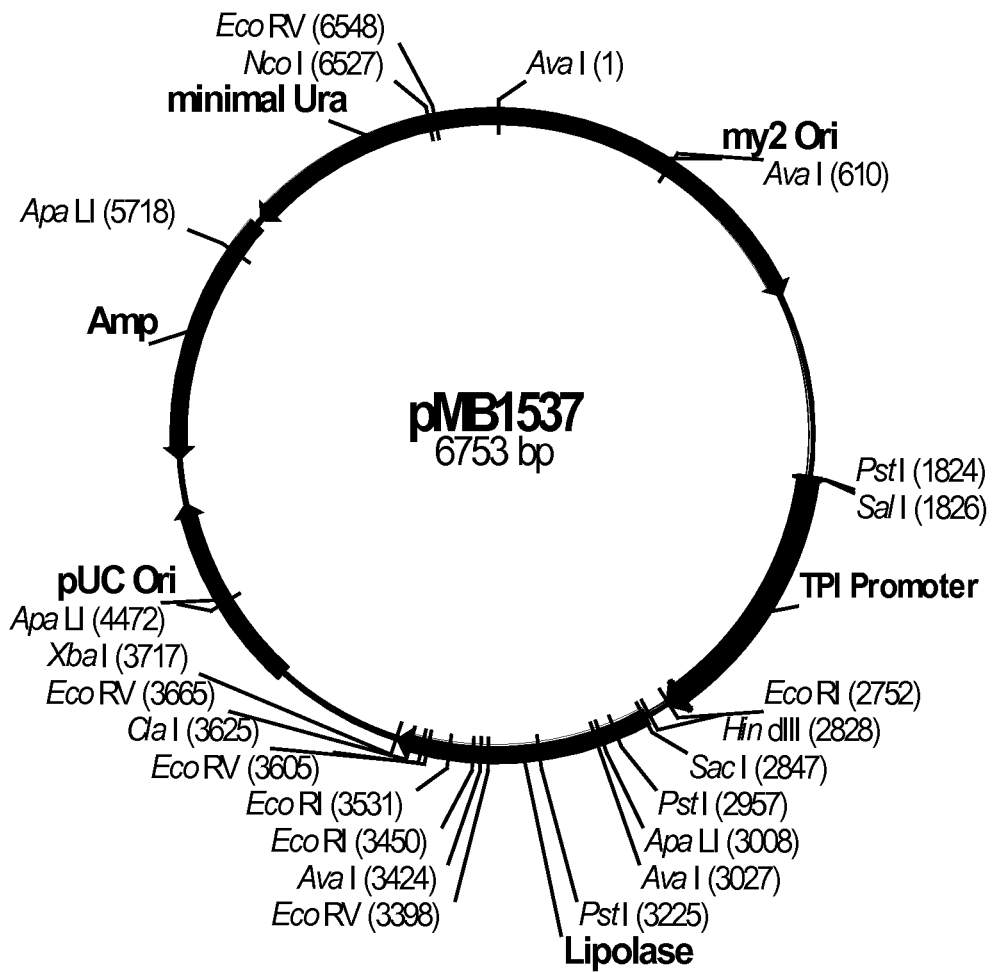
FIG. 2 shows a restriction map of pMB1537.

One yeast clone from the procedure above was restreaked on SC ura minus plates and one single yeast colony was inoculated into 10 ml of SC ura minus medium in a 50 ml shake flask and incubated overnight at 30° C., 250 rpm. Two ml of culture broth was used in a plasmid preparation using a QIAPREP® Spin Miniprep Kit (QIAGEN Inc., Germany) for yeast plasmid preparation. The plasmid was later sequenced and the expected DNA sequence was verified. The plasmid was designated pMB1537 (FIG. 2).

Example 3

Construction of Expression Vector pBM126a

Plasmid pMB128a was digested with Age I and Eco RI, and plasmid pMB1537 was digested with Eco RI and Nde I, and the fragments, 265 bp and 661 bp, respectively, were purified by 1.8% and 0.7% agarose gel electrophoresis using TAE buffer in conjunction with a QIAQUICK® Gel Extraction Kit. To create the vector fragment, pMB1537 was digested with Age I and Nde I. The resulting 5148 bp fragment was purified by 0.7% agarose gel electrophoresis using TAE buffer in conjunction with a QIAQUICK® Gel Extraction Kit.

Figure 3:
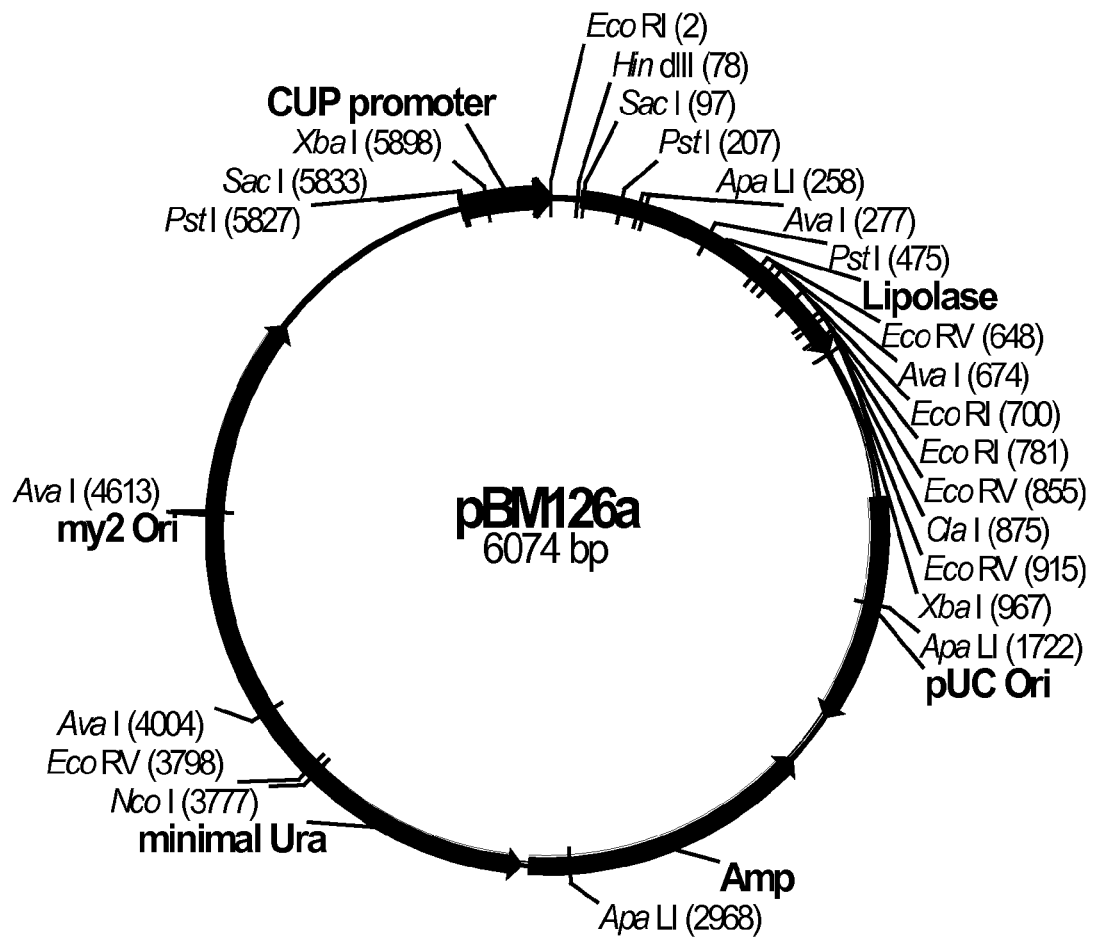

All three fragments were subsequently ligated using a Rapid DNA Ligation Kit (Roche Diagnostics Corporation, Indianapolis, Ind., USA). Two µl of the reaction were used to transform *E. coli* XL10-GOLD® Ultracompetent Cells (Stratagene, La Jolla, Calif., USA) according to manufacturer's instructions. Plasmid DNA was prepared from *E. coli* transformants using a BioRobot 9600. Isolated plasmids containing an insert were sequenced using 1 µl of plasmid template, 1.6 ng of M13 primer (forward or reverse), and water to 6 µl. The resulting plasmid identified as having the correct sequence was designated pBM126a (FIG. 3).

Example 4

Construction of Expression Vector pMB1539

Plasmid pMB1539 was constructed to contain a gene encoding a *Thermomyces lanuginosus* lipase variant (SEQ ID NO: 9 is the DNA sequence and SEQ ID NO: 10 is the deduced amino acid sequence) under control of the TPI promoter.

A gene fragment containing the *Thermomyces lanuginosus* lipase variant gene was prepared by PCR using pENi1298 (WO 00/24883) containing the *Thermomyces lanuginosus* wild-type lipase gene (SEQ ID NO: 7) as template using an EXPAND® High Fidelity PCR System, and primers 349699 and 353031, shown below.

```
Primer 349699:
                                        (SEQ ID NO: 17)
5'-CAAGAAGATTACAAACTATCAATTTCATACACAATATAAACGATTAA
AAGAAAGCTTCACCATGAGGAGCTCCCTTGTGCTGTTCTTTGTCT
CTG-3'

Primer 353031:
                                        (SEQ ID NO: 18)
5'-GAGGGCGTGAATGTAAGCGTGACATAACTAATTACATGATGCGGCCC
TCTAGATTATCAAAGACATGTCCCAATTAACCCGAAGTAC-3'
```

The PCR amplification reaction mixture contained approximately 50 ng of pENi1298 plasmid DNA, 1 µl of primer 349699 (50 pmol/µl), 1 µl of primer 353031 (50 pmol/µl), 5 µl of 10×PCR buffer (Roche, Indianapolis, Ind., USA) with 15 mM $MgCl_2$, 1 µl of dNTP mix (10 mM each), 40.25 µl of water, and 0.75 µl (3.5 U/µl) of DNA polymerase mix (Roche, Indianapolis, Ind., USA). An PTC Peltier Thermal Cycler was used to amplify the fragment programmed for 1 cycle at 94° C. for 2 minutes; 10 cycles each at 94° C. for 15 seconds, 55° C. for 30 seconds, and 72° C. for 15 seconds; 15 cycles each at 94° C. for 15 seconds, 55° C. for 30 seconds, and 72° C. for 15 seconds plus a 5 second elongation at each successive cycle; 1 cycle at 72° C. for 7 minutes; and a 10° C. hold.

After PCR amplification, a DNA fragment of 993 bp was purified using a GFX® PCR DNA and Gel Band Purification Kit. The resulting fragment (100 ng) was mixed with the pSTED226 vector fragment (100 ng) described in Example 2 and transformed into electrocompetent *Saccharomyces cerevisiae* JG169 cells by electroporation using a GENE PULSER® and Pulse Controller at 1.5 kvolts with a 2 mm gap cuvette according to the manufacturer's procedure. Transformed cells were then plated onto yeast ura minus selection plates and incubated for 5 days at 30° C.

Figure 4:
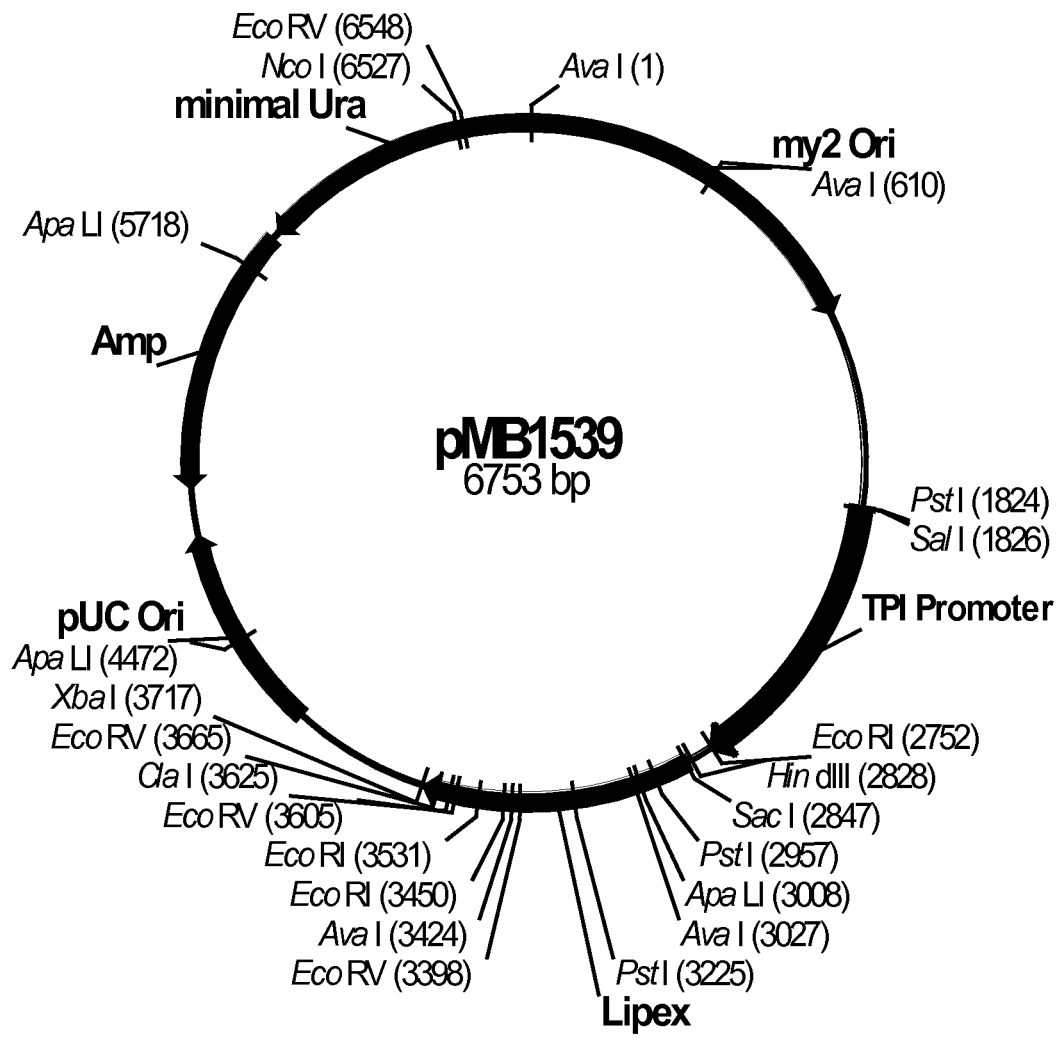
FIG. 4 shows a restriction map of pMB1539.

One yeast clone from the procedure above was restreaked on SC ura minus plates and one single yeast colony was used to inoculate 10 ml of SC ura minus medium in a 50 ml shake flask and incubated overnight at 30° C., 250 rpm. From this culture 2 ml of culture broth were used in a plasmid preparation using a QIAPREP® Spin Miniprep Kit for yeast plasmid preparation. The plasmid was later sequenced and the expected DNA sequence was verified. The plasmid was designated pMB1539 (FIG. 4).

Example 5

Construction of Expression Vector pJLin168

Figure 5:
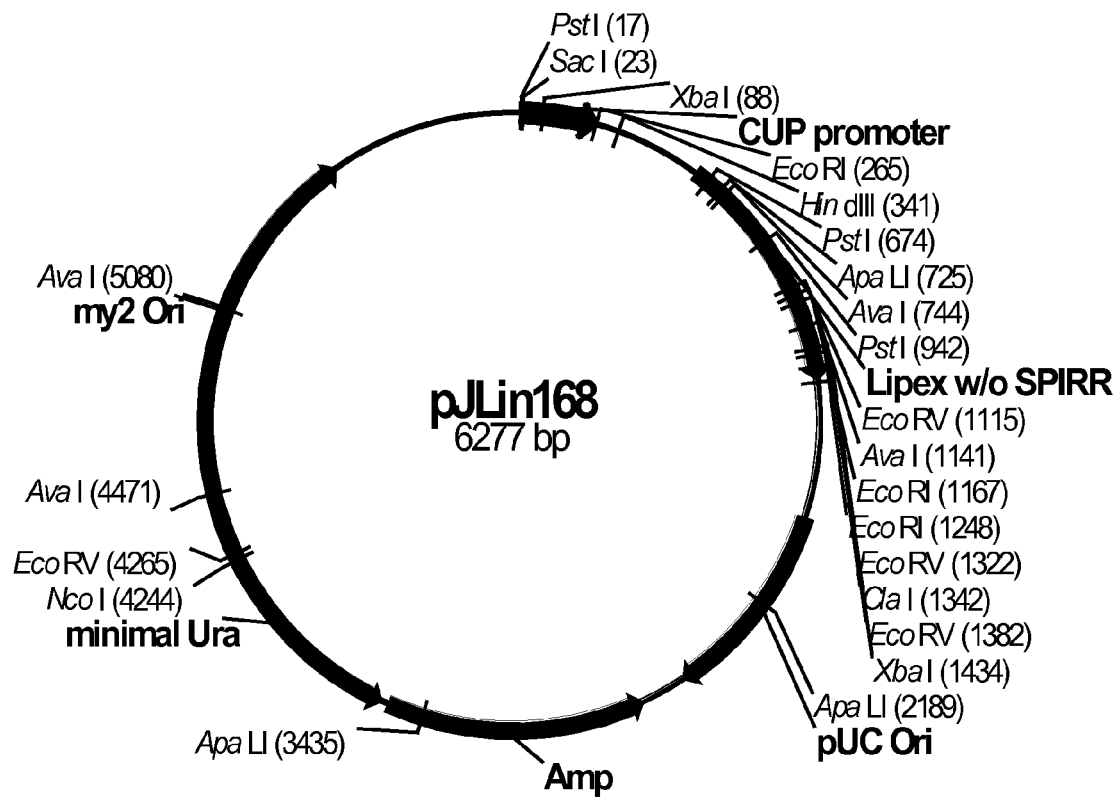
FIG. 5 shows a restriction map of pJLin168.

Construction of a *Thermomyces lanuginosus* lipase variant expression vector utilizing the CUP1 promoter was accomplished by swapping the *Thermomyces lanuginosus* wild-type lipase gene in pBM126a (containing the *Thermomyces lanuginosus* wild-type lipase gene under control of CUP1 promoter) with the *Thermomyces lanuginosus* lipase variant gene from pMB1539. First, both pBM126a and pMB1539 were digested with Hind III and Mlu I, and a 5 kb fragment from pBM126a and a 1.1 kb fragment from pMB1539 were gel-purified using a QIAQUICK® Gel Extraction Kit. Both fragments were subsequently ligated using a Rapid DNA Ligation Kit in molar ratios of vector:insert at 1:2, 1:3, and 1:4 with the vector amount set at 50 ng. The resulting plasmid, designated pJLin168 (FIG. 5), contained the *Thermomyces lanuginosus* lipase variant gene under control of the CUP1 promoter.

Example 6

Construction of Expression Vectors pBM142c and pBM143b

The following primers were designed to remove the last five codons encoding amino acids SPIRR (SEQ ID NO: 36) from the propeptide sequence of the *Thermomyces lanuginosus* variant lipase in pJLin168 using a QUIKCHANGE® Site-Directed Mutagenesis Kit (Stratagene, La Jolla, Calif., USA):

```
Primer 998570:
                                    (SEQ ID NO: 19)
5'-CTCTGCGTGGACGGCCTTGGCCGAGGTCTCGCAGGATCTGTTT
AAC-3'

Primer 998571:
                                    (SEQ ID NO: 20)
5'-TTAAACAGATCCTGCGAGACCTCGGCCAAGGCCGTCCACGCA
GAG-3'
```

Figure 6:
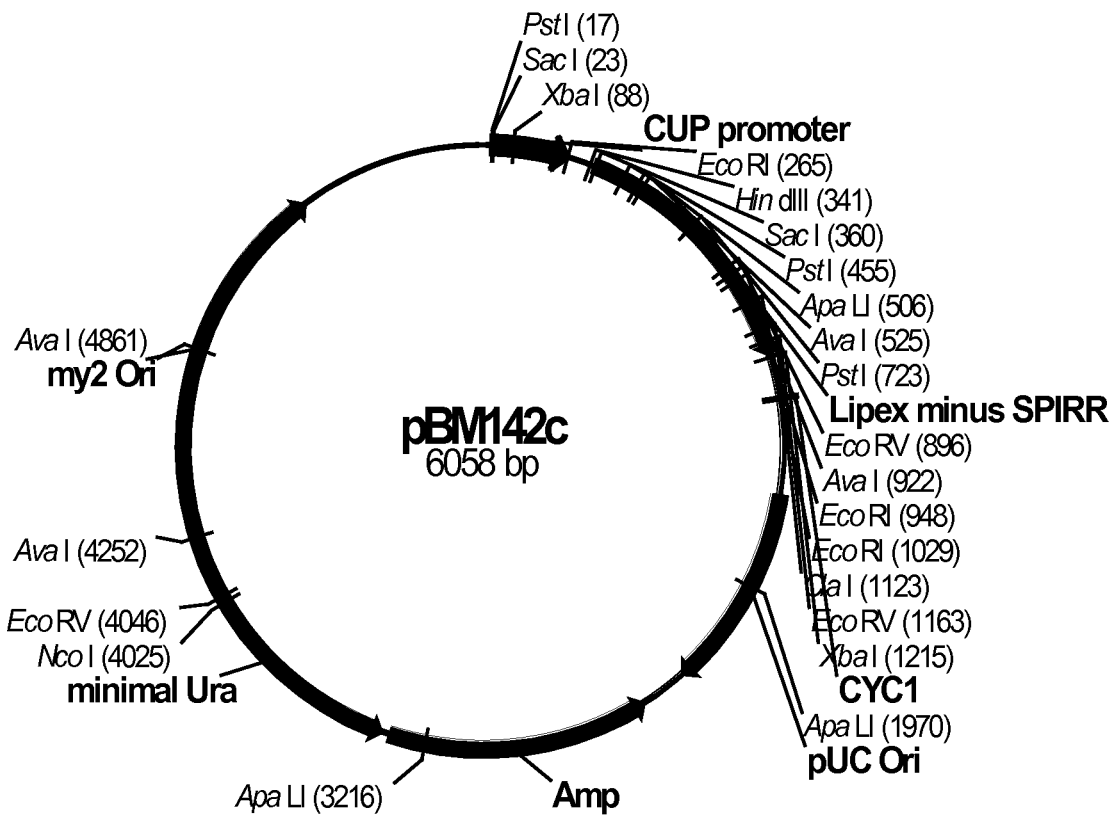
FIG. 6 shows a restriction map of pBM142c.

One hundred picomoles of each primer were used in a PCR reaction containing 73 ng of pJLin168, 1× QUIKCHANGE® reaction buffer (Stratagene, La Jolla, Calif., USA), 4 μl of QUIKSOLUTION® (Stratagene, La Jolla, Calif., USA), 1 μl of XL dNTP mix (Stratagene, La Jolla, Calif., USA), and 1 μl of 2.5 U/μl PfuUltra™ DNA polymerase (Stratagene, La Jolla, Calif., USA), in a final volume of 50 μl. An EPPENDORF® MASTERCYCLER® was programmed for one cycle at 95° C. for 1 minute; 18 cycles each at 95° C. for 50 seconds, 60° C. for 50 seconds, and 68° C. for 6 minutes; and a 10° C. hold. One microliter of Dpn I was added directly to the amplification reaction and incubated at 37° C. for 1 hour. A 2 μl volume of the Dpn I digestion reaction was used to transform *E. coli* XL10-GOLD® Ultracompetent Cells (Stratagene, La Jolla, Calif., USA) according to the manufacturer's instructions. One of the clones without 15 bp corresponding to the SPIRR-coding region was confirmed by DNA sequencing and was designated pBM142c (FIG. 6).

Figure 7:
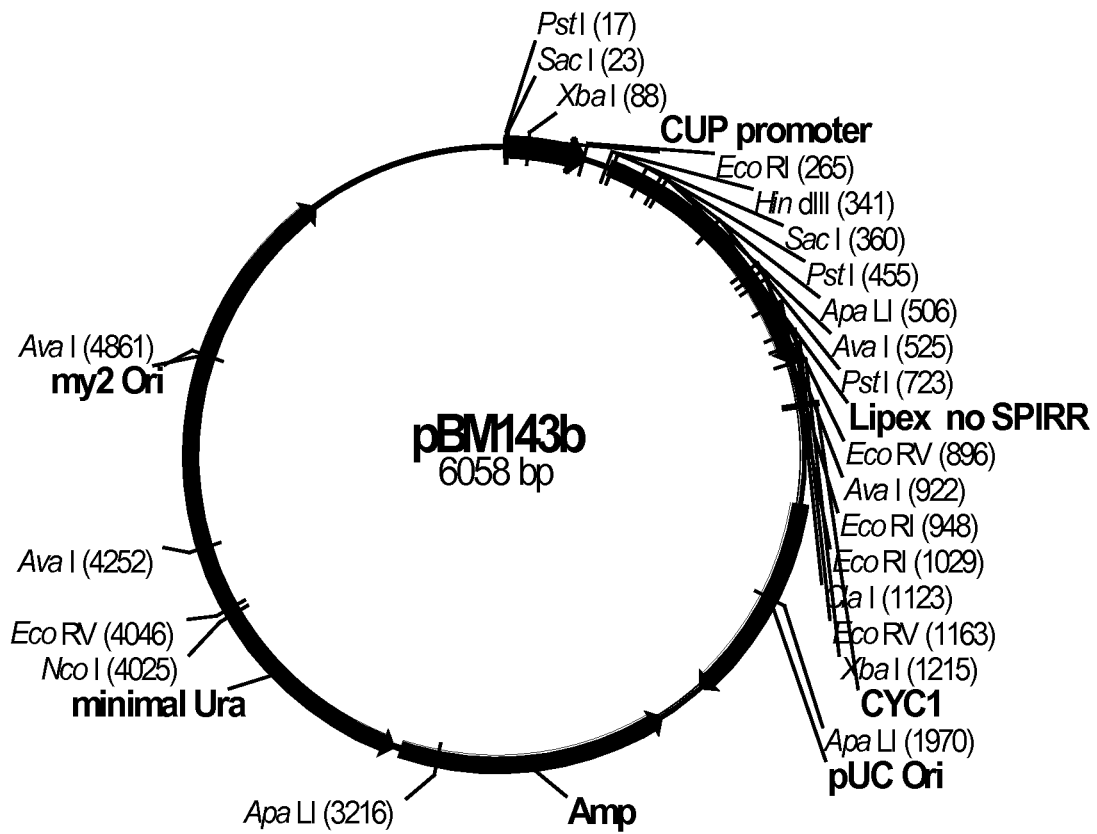
FIG. 7 shows a restriction map of pBM143b.

To avoid additional mutations being generated in pBM142c, the 5' region of *Thermomyces lanuginosus* variant lipase gene from pBM142c was cloned back into pJLin168. Plasmid pBM142c was digested with Hind III and Nde I, and the 0.6 kb fragment was purified by 1.5% agarose gel electrophoresis using TAE buffer in conjunction with a QIAQUICK® Gel Extraction Kit. Plasmid pJLin168 was digested with Hind III and Nde I, and the resulting 5.5 kb fragment was purified by 0.7% agarose gel electrophoresis using TAE buffer in conjunction with a QIAQUICK® Gel Extraction Kit. The two fragments were subsequently ligated using a Rapid DNA Ligation Kit. The resulting expression plasmid, designated pBM143b (FIG. 7), contained the CUP1 promoter driving expression of *Thermomyces lanuginosus* variant lipase gene. Thus, the 22 amino acid signal/propeptide sequence was changed to 17 amino acids by removing the last five amino acids (SPIRR).

Example 7

Transformation of *Saccharomyces cerevisiae* with pJLin168 and pBM143b

Plasmids pJLin168 and pBM143b were transformed into *Saccharomyces cerevisiae* strain JG169 using a YEASTMAKER™ Yeast Transformation System (Clonetech, Palo Alto, Calif., USA) according to the manufacturer's instructions. Briefly, one colony of *Saccharomyces cerevisiae* JG169 was inoculated into 50 ml of YPD medium and incubated at 30° C. overnight on an orbital shaker at 250 rpm. When the cells reached an absorbance of 0.4 to 0.5 at 600 nm, the cells were centrifuged at 700×g for 5 minutes, the supernatant was discarded, and the pellet was resuspended in 30 ml of deionized water. After centrifugation at 700×g for 5 minutes, the cell pellet was resuspended in 1.5 ml of 1.1×TE/lithium acetate solution (110 mM lithium acetate, 11 mM Tris, pH 8, 1.1 mM EDTA). After centrifugation at 12,000×g in a microcentrifuge for 15 seconds, the cell pellet was resuspended in 600 μl of 1.1×TE/lithium acetate solution. After addition of approximately 0.5 μg of vector DNA, 250 μl of PEG/lithium acetate solution (40% PEG 4000, 0.1 M lithium acetate, 10 mM Tris-HCl, pH 8, 1 mM EDTA), and 5 μl of 10 mg/ml denatured Herring Testes Carrier DNA to 50 μl of competent cells, the mixtures were shaken at 550 rpm at 30° C. for 30 minutes, and cells were mixed by inversion every 10 minutes. A total volume of 20 μl of DMSO was added to each transformation mixture, and incubated at 42° C. for 15 minutes, and the mixture was inverted every 5 minutes. The transformation mixtures were centrifuged for 15 seconds at 12,000×g in a microcentrifuge, and the cells were resuspended in 1 ml of YPD PLUS™ Liquid Medium (YEASTMAKER® Yeast Transformation System, Clonetech, Palo Alto, Calif., USA) and shaken at 550 rpm and 30° C. for 90 minutes. After centrifugation at 13,000×g, the cells were washed with 1 ml of 0.9% NaCl solution and resuspended in 1 ml of yeast ura minus selection medium in the presence of 15% glycerol. Fifty microliters of each transformation reaction were plated in duplicate onto yeast ura minus selection plates and incubated at 30° C. until colonies appeared.

Example 8

Evaluation of Expression of the *Thermomyces lanuginosus* Lipase Variant with Plasmids pJLin168 and pBM143b Expression of the *Thermomyces lanuginosus* lipase variant from pJLin168 and pBM143b was evaluated in shake flasks. Five representative *Saccharomyces cerevisiae* JG169 transformants, containing pJLin168 or pBM143b, from Example 7, were grown in duplicate shake flask cultures containing 25 ml of "original" medium. Shake flask samples were harvested 4, 5, and 7 days. Lipase activities of culture supernatants were measured using p-nitrophenyl butyrate as a substrate in the following assay: Culture supernatants were initially diluted $\frac{1}{15}$-fold in 0.1 M MOPS, 4 mM $CaCl_2$, 0.01% Triton X-100 buffer, pH 7.5 (sample buffer), followed by serial dilution from 0-fold to $\frac{1}{3}$-fold to $\frac{1}{5}$-fold of the diluted sample. A LIPOLASE™ standard (Novozymes NS, Bagsværd, Denmark) was diluted using two-fold steps starting with a 1.0 LU/ml concentration and ending with a 0.125 LU/ml concentration in the sample buffer. A total of 20 µl of each dilution, including the standard, were transferred to a 96-well flat bottom plate. Two hundred microliters of a p-nitrophenyl butyrate substrate solution (the ratio of p-nitrophenyl butyrate to DMSO to 0.1 M MOPS pH 7.5 was 1:99:400) was added to each well, and then incubated at 25° C. for 15 minutes. Upon completion of the incubation, the absorbance at 405 nm was measured for the 96-well plate. Sample concentrations were determined by extrapolation from the generated standard curve.

Figure 8:
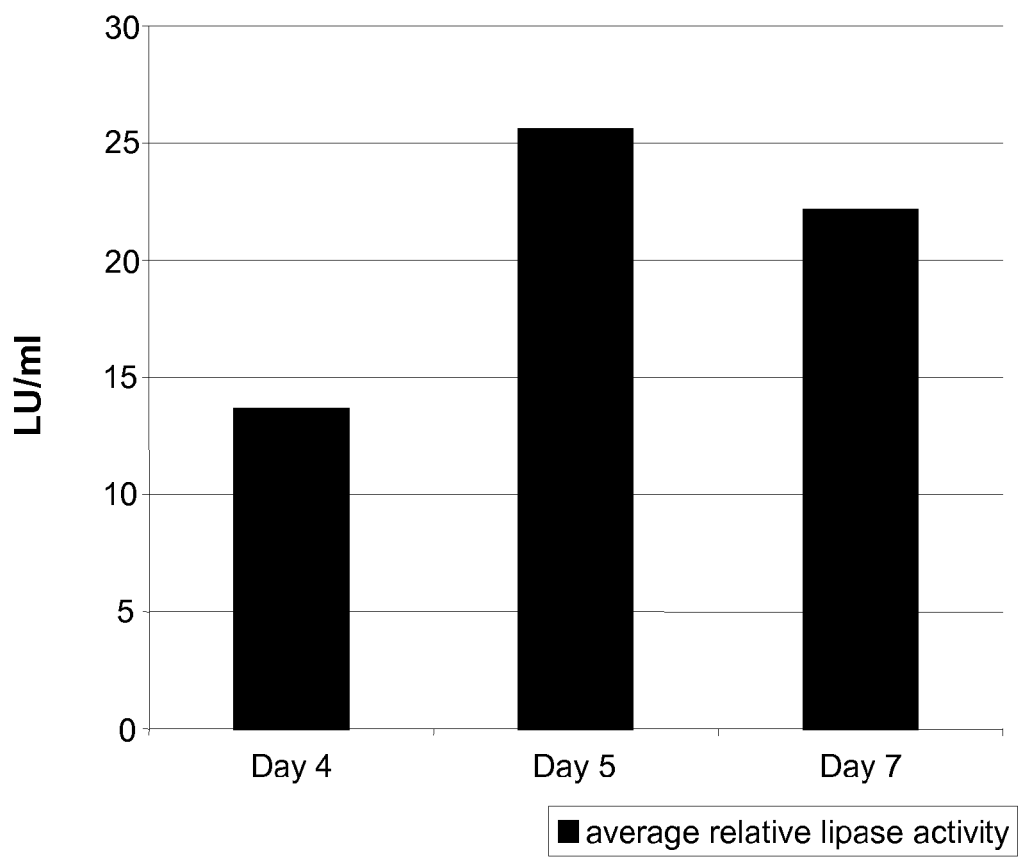
FIG. 8 shows the average relative lipase activities for pJLin168 transformants.
Figure 9:
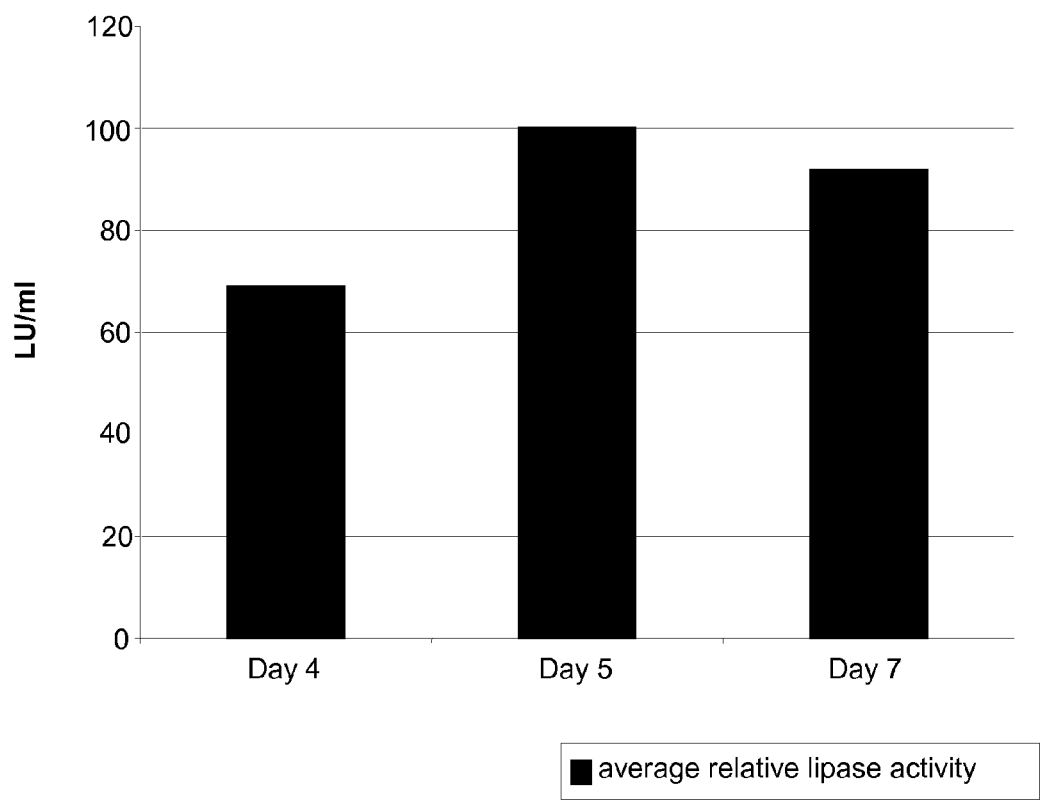
FIG. 9 shows the average relative lipase activities for pBM143b transformants.

The average relative lipase activities for pJLin168 transformants were 14, 26, and 22, for samples taken from day 4, day 5, and day 7, respectively (FIG. 8). The average relative lipase activities for pBM143b transformants were 69, 100, and 92, for samples taken from day 4, day 5, and day 6, respectively (FIG. 9).

To confirm the lipase activity assay results, SDS-PAGE was performed on supernatants from the samples. Twenty microliters of culture supernatant from two shake flask samples taken on day 5 were mixed with Laemmli Sample buffer (Bio-Rad Laboratories, Inc., Hercules, Calif., USA) in a 1:2 ratio. After boiling for 2 minutes, samples were loaded onto a 10-20% SDS-PAGE gel (Bio-Rad Laboratories, Inc., Hercules, Calif., USA) along with 15 µl of PRECISION PLUS PROTEIN™ standards (Bio-Rad Laboratories, Inc., Hercules, Calif., USA). Gels were run in 1×Tris-glycine-SDS running buffer (Bio-Rad Laboratories, Inc., Hercules, Calif., USA) at 200 V for 1 hour. The gels were then rinsed 3 times with water for 5 minutes each, and stained with BIO-SAFE™ Coomassie Stain (Bio-Rad Laboratories, Inc., Hercules, Calif., USA) for 1 hour followed by destaining with water for at least 30 minutes.

The SDS-PAGE results showed that the increased lipase activity observed for the pBM143b transformants corresponded to increased protein levels.

Example 9

Mutagenesis of *Thermomyces lanuginosus* Lipase Variant Signal Sequence

Plasmid pMB1537 containing the *Thermomyces lanuginosus* wild-type lipase gene was used to construct a random mutagenized library of the *Thermomyces lanuginosus* lipase signal peptide. A random mutagenized PCR fragment of the signal peptide coding sequence and flanking DNA regions was amplified by PCR using an EXPAND® High Fidelity PCR System and the primers (DNA-Technology, Aarhus, Denmark) shown below.

```
Primer 309787:
                                         (SEQ ID NO: 21)
5'-CTAGGAACCCATCAGGTTGGTGGAAG-3'

Primer 373172:
                                         (SEQ ID NO: 22)
5'-CTGTGCAAAGAGATTGAACTGGTTAAACAGATCCTGCGANNNNNNNN
NNNNNNNNNNNNNNNNNNNNNNNNNNNNNNNNNNNNNNNNNNNNNCATG
GTGAAGCTTTCTTTTAA-3'
``` where N at positions 41, 50, 51, 60, 64, 66, 68, 70, 71, 72, 74, 75, 77, 80, 82, 83, and 87 of SEQ ID NO: 22 is 99% A and 1% G, C or T;

N at positions 40, 46, 47, 52, 53, 56, 62, 65, 67, 73, 78, 84, 85, 86, and 88 of SEQ ID NO: 22 is 99% G and 1% A, C, or T;

N at positions 42, 43, 45, 48, 49, 54, 55, 58, 59, 61, 63, 69, 76, 79, 81, 89, 91, and 92 of SEQ ID NO: 22 is 99% C and 1% A, G, or T; and N at positions 44, 57, 90, and 93 of SEQ ID NO: 22 is 99% T and 1% A, C, or G.

The primer introducing the diversity was designed after the following rules: The wild-type base at the randomized positions was always present at 99% and the other three bases were present at 1% and all three were equally represented.

The mutagenized fragment of the signal peptide coding sequence was amplified by PCR using an EXPAND® High Fidelity PCR System. The PCR amplification reaction mixture contained approximately 50 ng of pMB1537, 1 µl of primer 309787 (50 pmol/µl), 1 µl of primer 373172 (50 pmol/µl), 5 µl of 10×PCR buffer (Roche, Indianapolis, Ind., USA) with 15 mM $MgCl_2$, 1 µl of dNTP mix (10 mM each), 40.25 µl of water, and 0.75 µl (3.5 U/µl) of DNA polymerase mix (Roche, Indianapolis, Ind., USA). A PTC Peltier Thermal Cycler was used to amplify the fragment programmed for 1 cycle at 94° C. for 2 minutes; 10 cycles each at 94° C. for 15 seconds, 55° C. for 30 seconds, and 72° C. for 15 seconds; 15 cycles each at 94° C. for 15 seconds, 55° C. for 30 seconds, and 72° C. for 15 seconds plus a 5 second elongation at each successive cycle; 1 cycle at 72° C. for 7 minutes; and a 10° C. hold.

A gene fragment of the *Thermomyces lanuginosus* wild-type lipase gene was prepared by PCR using pMB1537 as template in a PCR reaction using an EXPAND® High Fidelity PCR System. The primers used in the PCR were primers 309787 and 373172 described above.

After PCR amplification, a PCR fragment of 600 bp was purified using a GFX® PCR DNA and Gel Band Purification Kit according to the manufacturer's protocol and eluted in 50 µl of 10 mM Tris-HCl pH 8.0.

Plasmid pMB1537 was linearized by digestion with Sac I at a DNA position within the signal peptide coding sequence. The linearized vector was used as the recipient DNA in a transformation of *Saccharomyces cerevisiae* JG169 using a PCR fragment of the signal peptide coding sequence with flanking DNA regions (100% homologous to the recipient DNA of the recipient plasmid) as the donor DNA.

Specifically, approximately 3 µg of Sac I digested pMB1537 together with approximately 1 µg of the 600 bp PCR fragment were electroporated into 100 µl of electrocompetent *Saccharomyces cerevisiae* JG169 cells using a GENE PULSER® and Pulse Controller at 1.5 kvolts with a 2 mm gap cuvette. After electroporation the transformed cells were supplied with 1 ml of 1 M sorbitol, and incubated for 1 hour at 30°

C. after which 1.1 ml were plated onto SC ura minus plates supplemented with 100 µg of ampicillin per ml.

A total of 8400 colonies from the SC ura minus plates supplemented with 100 µg of ampicillin per ml were picked and transferred to 96-well polystyrene microwell plates, applying the picked clones to the wells in rows B-H and columns 1-12 leaving row A free, which was inoculated with the wild-type plasmid construct in *Saccharomyces cerevisiae* JG169 as the wild-type reference. All wells contained SD Medium-URA with 40 mg of adenine added per liter (called SDMUA) (following recommendations from the manufacturer, Qbiogene, Inc., BIO 101® System, supplied by AH Diagnostics, Aarhus, Denmark). The plates were incubated at 30° C. and 250 rpm for 5 days. After 5 days the plates were kept at 4° C. before measuring lipase activity using a p-nitrophenyl valerate assay described below.

Lipase activities of culture supernatants were measured using p-nitrophenyl valerate as a substrate in the following assay. Culture supernatants were diluted in 50 mM Tris pH 7, 10 mM $CaCl_2$, 0.4% Triton X-100 buffer (dilution buffer). A LIPOLASE™ standard (Novozymes NS, Bagsværd, Denmark) was diluted using two-fold steps starting with a 1.0 LU/ml concentration and ending with a 0.125 LU/ml concentration in the sample buffer. In polystyrene microwell plates, 10 µl of supernatant were mixed with 90 µl of the dilution buffer. One hundred microliters of a p-nitrophenyl valerate substrate solution (117 µl of p-nitrophenyl valerate dissolved in 10 ml of isopropanol) was added to each well, briefly mixed, and then the absorbance at 405 nm was measured for 3 minutes every 12 seconds. The assay data was evaluated to identify all samples having higher activity than the pMB1539 construct in *Saccharomyces cerevisiae* JG169 (in the A-row wells).

All clones with higher activity than the reference were collected as positive hits, which were reanalyzed in the same set-up and all clones still having higher activity than the reference were used as inoculation material with fresh SDMUA medium in microwell plates. The A-row was again used for the reference strain. The plates were incubated as above, and analyzed as described above.

All clones with higher activity than the reference were removed from their wells and restreaked on SC-agar plates. Single colonies of all clones were collected for regrowth in microwell plates in 200 µl of SDMUA medium and 50 ml tubes containing 10 ml of SDMUA medium and incubated at 30° C. for 5 days after which yields were compared to that of the reference strain using the p-nitrophenyl valerate assay described above.

Each clone was grown in three adjacent microwells and 3 individual 50 ml tubes. Mean values of the three growth experiments were used for the comparison of activity levels.

Finally the clones with the highest lipase activity in both microwell plates and 50 ml tubes were inoculated in shake flasks (250 ml conical baffled shake flasks with two baffles) containing 10 ml of SDMUA medium and incubated at 250 rpm for 5 days at 30° C. Supernatants were assayed for lipase activity using the p-nitrophenyl valerate assay described above. Clones with the highest lipase activity were DNA sequenced.

The clone showing the highest activity was designated MB1665, which had a R2K substitution in the signal peptide of the lipase (second codon of the signal peptide was altered from AGG to AAG).

By using the same principle as described in Example 4, DNA encoding this signal peptide was transferred to the pMB1539 construct encoding the *Thermomyces lanuginosus* lipase variant. In this case the smaller PCR fragment was made using the same procedure as described in Example 4. However, the larger fragment was made also according to Example 4 but using plasmid DNA from MB1539 as the template. GAP-repair and transformation of the *Saccharomyces cerevisiae* JG169 was performed as described above. This cloning resulted in a clone with higher expression of the *Thermomyces lanuginosus* lipase variant. This clone was designated *Saccharomyces cerevisiae* MB1681.

Figure 10:
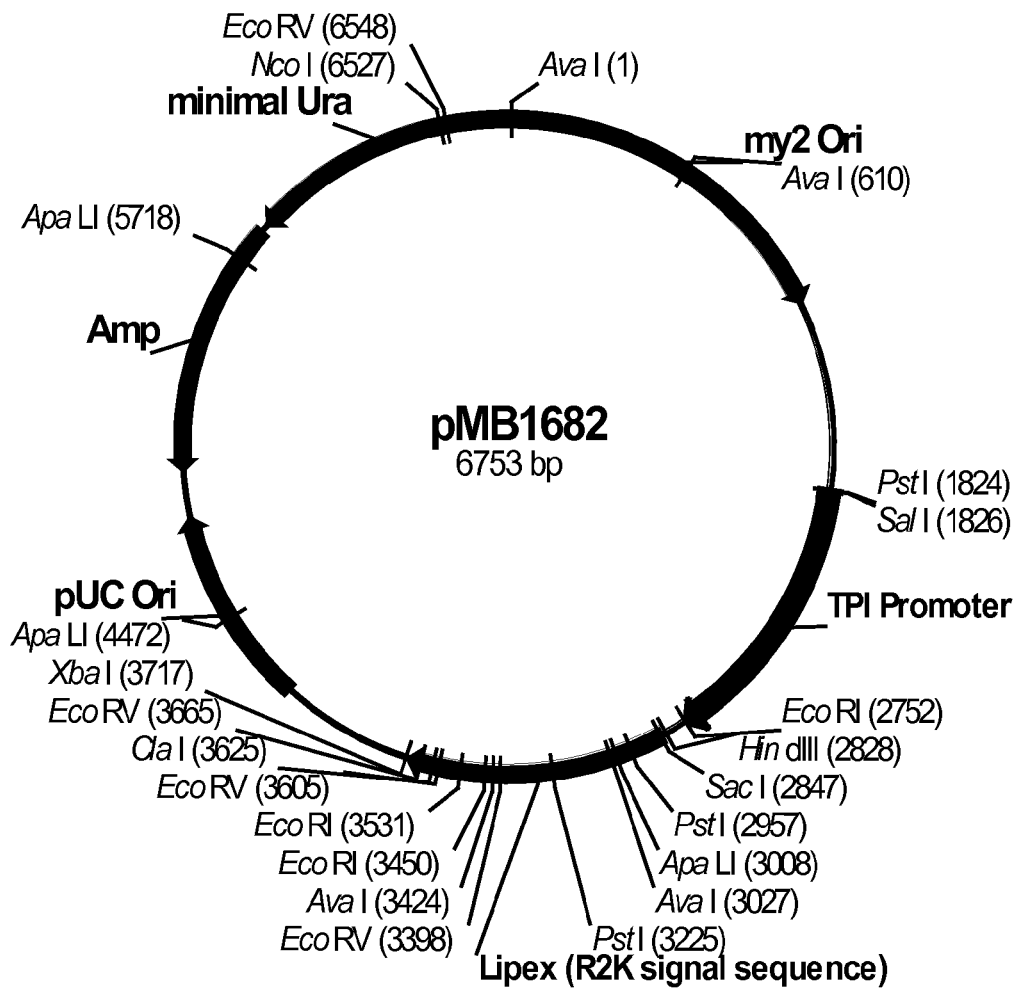
FIG. 10 shows a restriction map of pMB1682.

*Saccharomyces cerevisiae* MB1681 cell material from a SC-agar plate (grown 5 days at 30° C.) was used to inoculate 10 ml of SC ura minus medium in a 50 ml shake flask and incubated overnight at 30° C., 250 rpm. From this culture 2 ml of culture broth was used in a plasmid preparation using a QIAPREP® Spin Miniprep Kit for yeast plasmid preparation The purified plasmid was transformed into *E. coli* Top10F' (Invitrogen, Carlsbad, Calif., USA) according to manufacturer's instructions. Transformed *E. coli* cells were plated onto LB plates supplemented with 100 µg of ampicillin per ml. A single colony was isolated, restreaked, inoculated into LB medium, and incubated overnight at 30° C. One ml of the overnight culture was used for plasmid preparation using a QIAPREP® Spin Miniprep Kit. Finally, the isolated plasmid was used as template for DNA sequencing, verifying the sequence of the variant signal sequence (SEQ ID NO: 3) and the *Thermomyces lanuginosus* lipase variant coding region (SEQ ID NO: 9 with the deduced amino acid sequence of SEQ ID NO: 10). The resulting plasmid was designated pMB1682 (FIG. 10). Plasmid pMB1682 comprised the TPI promoter and the *Thermomyces lanuginosus* lipase variant coding region (without SPIRR (SEQ ID NO: 36) with a R2K change).

Example 10

Construction of pJLin195

Plasmid pJLin195 was constructed to contain the *Thermomyces lanuginosus* lipase variant (with signal sequence containing a R2K change and without SPIRR (SEQ ID NO: 36)) expression vector utilizing the *Saccharomyces cerevisiae* CUP1 promoter.

Figure 11:
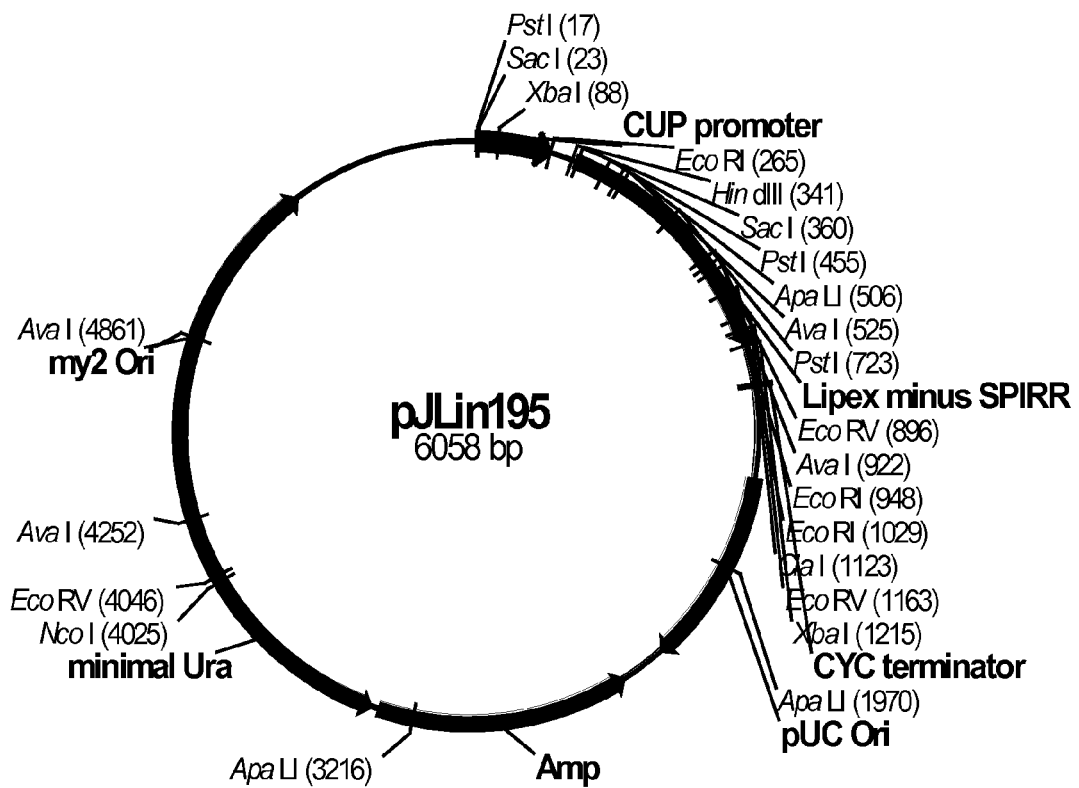
FIG. 11 shows a restriction map of pJLin195.

The Hind III-Nde I fragment of pMB1682 was cloned into pBM143b digested with Hind III and Nde I, replacing the coding sequence of the second amino acid Arg (AGG) with the coding sequence of Lys (AAG). Both pMB1682 and pBM143b were digested with Hind III and Nde I, and a 1 kb fragment from pMB1682 and a 5 kb fragment from pBM143b were gel extracted with a QIAQUICK® Gel Extraction column. The fragments were ligated together in a molar ratio of vector to insert at 1:2, 1:1, and 3:1 with a vector amount of 50 ng using a Rapid DNA Ligation Kit according to the manufacturer's instructions. The resulting plasmid, confirmed by DNA sequencing, was designated pJLin195 (FIG. 11).

Example 11

Transformation of *Saccharomyces cerevisiae* with pJLin195 and pBM143b

Plasmid pBM143b and pJLin195 were separately transformed into *Saccharomyces cerevisiae* strain JG169 as described in Example 7, except YPD medium was used in place of YPD PLUS™ Liquid Medium. Also, after washing with 0.9% NaCl, 200 µl of the cell suspension in ura minus medium was plated directly to yeast ura selection plates. Colonies were streaked onto yeast ura selection plates, and two colonies for each transformant were grown and broths were used to determine lipase activities.

Purified *Saccharomyces cerevisiae* JG169 transformants containing pBM143b or pJLin195 (at least 10 for each construct) were inoculated in duplicate into 180 µl of ura selection medium in 96 well plates and incubated at 30° C., 250 rpm overnight. The overnight cultures were then diluted 100-fold in 180 µl of CUP minus ura medium and grown for 5 days at 30° C., 250 rpm. *Saccharomyces cerevisiae* JG169, grown in the same medium except in the presence of 10 mM uridine, was included as a negative control.

Figure 12:
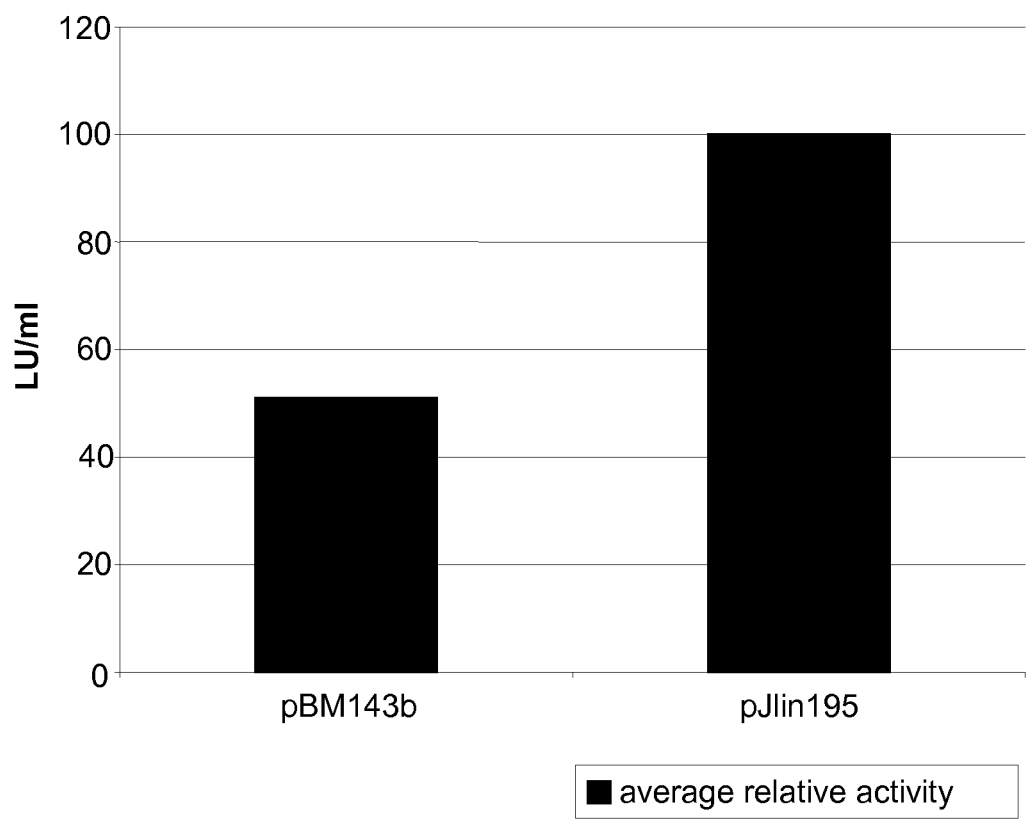
FIG. 12 shows the average relative lipase activities for pBM143b and pJLin195 transformants.

Lipase activities were determined as described in Example 8. The relative average lipase activities for pBM143b and pJLin195 transformants were 51 and 100, respectively (FIG. 12). The t-test showed that activities of the pJLin195 transformants were significantly different from the pBM143b transformants. The results suggested that the R2K signal sequence improved the yield of the *Thermomyces lanuginosus* lipase variant 2.1-fold.

Example 12

Evaluating Expression of *Thermomyces lanuginosus* Lipase Variant with Plasmids pJLin195 and pBM143b in Shake Flasks To perform shake flask analysis, representative pBM143b and pJLin195 transformants were inoculated into 2 ml of ura selection medium and incubated at 30° C., 250 rpm overnight. The overnight cultures were then diluted 200-fold in 25 ml of CUP minus ura medium in 125 ml plastic shake flasks and grown for 6 days at 30° C., 250 rpm. Samples were taken at 5 and 6 days and centrifuged at 12,000×g in a microcentrifuge for 10 seconds. The supernatants were assayed for lipase activity as described in Example 8.

Figure 13:
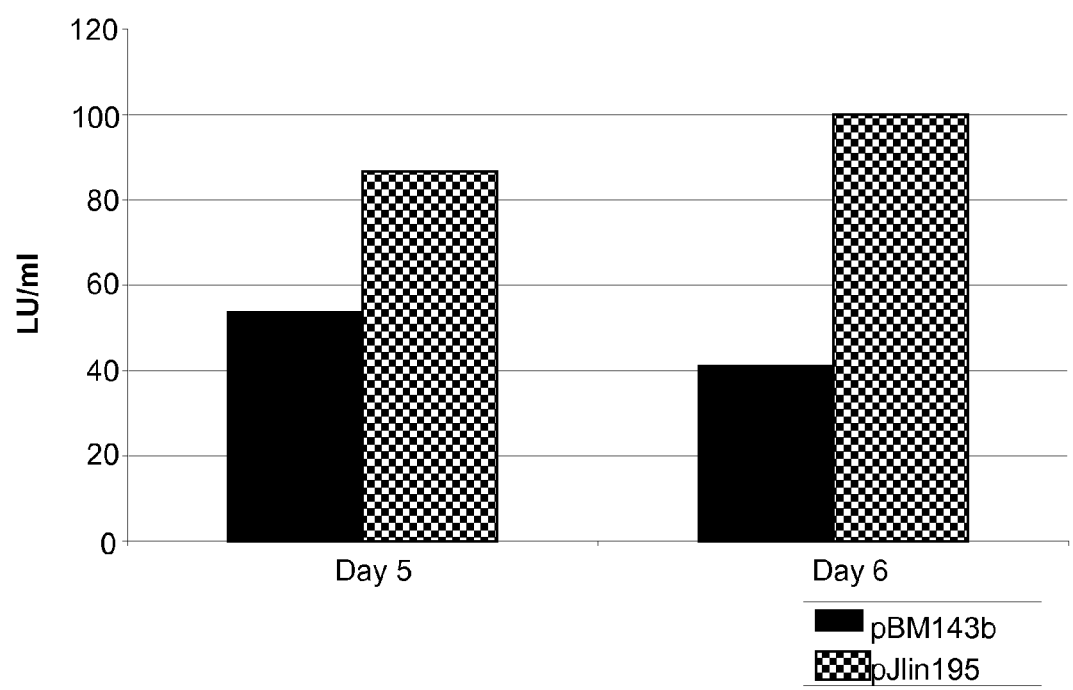
FIG. 13 shows the average relative lipase activities for pBM143b transformants in shake flasks.

The results showed that lipase activities peaked around days 5 to 6 (FIG. 13). Overall lipase activities were higher on day 5 when grown in shake flasks when compared with 96 well samples. On average the *Thermomyces lanuginosus* lipase variant with the R2K signal sequence showed 2-fold higher relative lipase activity (wild-type *Thermomyces lanuginosus* lipase variant as 1) on day 5. Therefore, 25 ml shake flasks showed similar results as cultures grown in 96 well plates. *Thermomyces lanuginosus* lipase variant with the R2K signal sequence showed slightly higher activity on day 6 when compared with day 5, so the improvement was even higher on day 6.

To confirm the lipase activity assay results, SDS-PAGE was performed on supernatants from the shake flask cultures as described in Example 8. The SDS-PAGE results showed that the intensities of the *Thermomyces lanuginosus* lipase variant bands from representative transformants were consistent with the lipase activity assay results.

Example 13

N-Terminal Sequence Analysis of *Thermomyces lanuginosus* Lipase Variant

N-terminal sequencing was performed on a Procise cLC Protein Sequencer (Applied Biosystems, Foster City, Calif., USA) with on-line capillary HPLC and liquid phase trifluoroacetic acid (TFA) delivery. Protein samples were electroblotted onto PVDF membranes (Invitrogen, San Diego, Calif., USA) from SDS-PAGE gels using 10 mM CAPS (3-[cyclohexylamino]-1-propanesulfonic acid) in 10% methanol, pH 11.0 for 2 hours at 25 volts on a NOVEX® XCell II (Invitrogen, San Diego, Calif., USA) with electroblotting gel apparatus or 2 hours at 100 volts on a CRITERION® gel apparatus fitted with a TRANS-BLOT® Transfer Cell (Bio-Rad Laboratories, Hercules, Calif., USA). PVDF membranes were stained with 0.1% Commassie Blue R-250 in 40% methanol/ 1% acetic acid for 20 seconds and de-stained in 50% methanol to observe the protein bands. Stained protein bands were excised and sequenced. Detection of phenylthiohydantoin-amino acids was accomplished by on-line capillary HPLC using 500 ml of Buffer A containing 3.5% tetrahydrofuran in water with 9 ml of the Premixa concentrate (Applied Biosystems, Foster City, Calif., USA) containing acetic acid, sodium acetate, and sodium hexanesulfonate and Solvent B2 containing acetonitrile/2-propanol. Data was collected and analyzed on a MACINTOSH® G4 processor using APPLIED BIOSYSTEMS® 610 Data Analysis software version 2.1a. Sequence determinations were made by visualizing chromatograms against a light source.

N-terminal sequencing analysis showed correct processing for *Thermomyces lanuginosus* lipase variant carrying the R2K variant signal sequence. The N-terminal sequence determined for transformants of pJLin195 was EVSQDLFNQFN (amino acids 1 to 11 of SEQ ID NO: 10).

Example 14

Construction of pJLin187

Plasmid pJLin187 was constructed by introducing a L269I change in the lipase gene from pJLin168, and by subcloning the lipase fragment into the *Aspergillus oryzae* expression vector pBM120a. PCR amplification was performed using gene-specific forward and reverse primers shown below.

```
Forward primer:
                                          (SEQ ID NO: 23)
5'-ACACAACTGGCCATGAGGAGCTCCCTTGTGCTGTTC-3'

Reverse primer:
                                          (SEQ ID NO: 24)
5'-AGTCACCTCTAGTTAATTAATTATCAAATACATGTCCCAA-3'
```

Bold letters represent coding sequence while italicized letters represent the Pac I site added to the 3' end of the *Thermomyces lanuginosus* lipase variant gene. The underlined AAT in the reverse primer indicates nucleotide changes to obtain L269I in the lipase gene. The remaining sequence is homologous to regions flanking the insertion site of pBM120a.

PCR amplification was performed using an EXPAND® High Fidelity PCR System according to manufacturer's instructions. Each PCR reaction contained 1 µl of pJLin168, 200 µM dNTPs, 1 µM forward and reverses primers, 1× reaction buffer, and 2.6 units of EXPAND® High Fidelity enzyme mix. The reaction was subjected to amplification using an EPPENDORF® MASTERCYCLER® programmed for 1 cycle at 94° C. for 2 minutes; 10 cycles each at 94° C. for 15 seconds, 58.3° C. for 30 seconds, and 72° C. for 1 minute and 15 seconds; 15 cycles each at 94° C. for 15 seconds, 58.3° C. for 30 seconds, and 72° C. for 1 minute and 15 seconds with 5 seconds cycle elongation for each successive cycle; and 1 cycle at 72° C. for 7 minutes. A 0.9 kb PCR product was purified using a QIAQUICK® PCR Purification Kit, and then cloned into pBM120a using an INFUSION® Cloning Kit (BD Biosciences, Palo Alto, Calif., USA). The INFUSION® cloning reaction was composed of 1× INFUSION® Buffer (BD Biosciences, Palo Alto, Calif., USA), 1×BSA (BD Biosciences, Palo Alto, Calif., USA), 1 µl of INFUSION® enzyme (diluted 1:10), 100 ng of pBM120a digested with Nco I and Pac I, and 50 ng of the purified PCR product containing the lipase gene in a total volume of 50 μl. The reaction was incubated at room temperature for 30 minutes.

Figure 14:
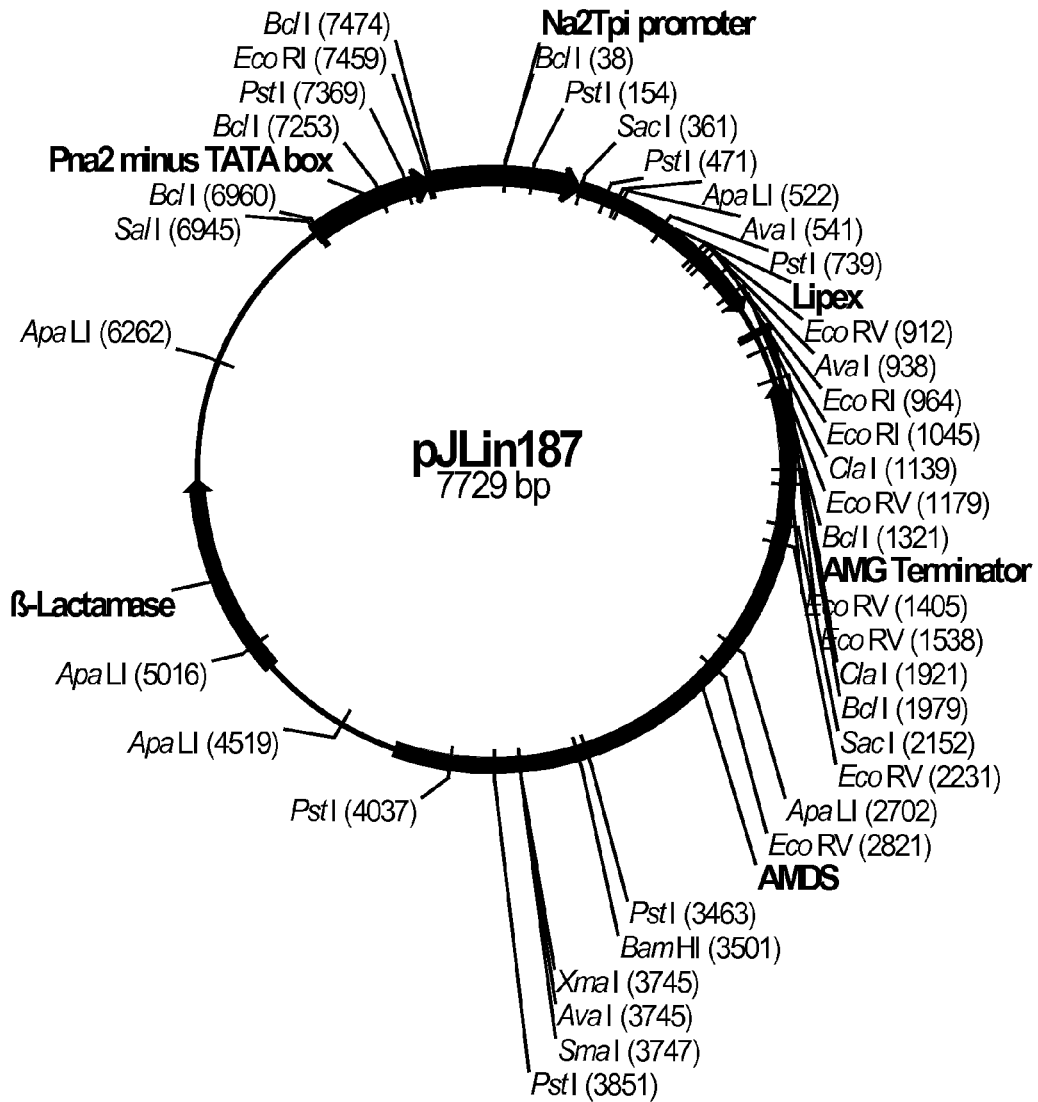
FIG. 14 shows a restriction map of pJLin187.

Two μl of the reaction was used to transform *E. coli* SOLO-PACK® Gold supercompetent cells (Stratagene, La Jolla, Calif., USA). One of the pBM120a plasmids containing the desired lipase sequence, which was confirmed by restriction digestion and sequencing analysis, was designated pJLin187 (FIG. 14).

Example 15

Construction of pBM120 Expression Vector

Plasmid pBM120a was constructed to obtain a plasmid containing the double NA2 promoter (NA2-NA2-tpi) for driving gene expression in *Aspergillus* species, and containing the ampicillin resistance gene for selection in *E. coli*.

Primers were designed to PCR amplify the double NA2 promoter from pJaL721 (WO 03/008575). Restriction enzyme sites Sal I and Nco I (underlined) were added for cloning the double promoter into the *Aspergillus* expression plasmid pAlLo1 (WO 2005/067531).

```
                                      (SEQ ID NO: 25)
5'-GTCGACATGGTGTTTTGATCATTTTA-3'

(SEQ ID NO: 26)
5'-CCATGGCCAGTTGTGTATATAGAGGA-3'
```

The fragment of interest was amplified by PCR using an EXPAND® High Fidelity PCR System. The PCR amplification reaction mixture contained 1 μl of 0.09 μg of pJaL721 per μl, 1 μl of each of the primers (50 pmol/μl), 5 μl of 10×PCR buffer with 15 mM MgCl$_2$, 1 μl of a dATP, dTTP, dGTP, and dCTP mix (10 mM each), 37.25 μl of water, and 0.75 μl of DNA polymerase mix (3.5 U/μl). To amplify the fragment, an EPPENDORF® MASTERCYCLER® was programmed for 1 cycle at 94° C. for 2 minutes; 10 cycles each at 94° C. for 15 seconds, 55° C. for 30 seconds, and 72° C. for 1.25 minutes; 15 cycles each at 94° C. for 15 seconds, 55° C. for 30 seconds, and 72° C. for 1.25 minutes plus a 5 second elongation at each successive cycle; 1 cycle at 72° C. for 7 minutes; and a 10° C. hold. Ten microliters of this PCR reaction was mixed with 1 μl of 10×DNA loading dye (25% glycerol, 10 mM Tris pH 7.0, 10 mM EDTA, 0.025% bromophenol blue, 0.025% xylene cyanol) and run on a 1.0% (w/v) agarose gel using TAE buffer. The 1128 bp PCR product was observed with UV light on a gel visualization system (Nucleotech, San Mateo, Calif., USA). The PCR product was directly ligated into pCR2.1-TOPO® according to the manufacturer's instructions. A 1 μl volume of fresh PCR product, 3 μl of double-distilled water, and 1 μl of the TOPO® cloning vector were mixed with a pipette and incubated at room temperature for 5 minutes.

After the incubation, 2 μl of the mixture was used to transform ONESHOT® TOP10 chemically competent *E. coli* cells (Invitrogen Corporation, Carlsbad, Calif., USA). A 2 μl volume of the ligation mixture was added to the *E. coli* cells and incubated on ice for 5 minutes. Subsequently, the cells were heat shocked for 30 seconds at 42° C., and then placed on ice for 2 minutes. A 250 μl volume of SOC medium was added to the cells and the mixture was incubated for 1 hour at 37° C. and 250 rpm. After the incubation the colonies were spread on 2×YT plates supplemented with 100 μg of ampicillin per ml and incubated at 37° C. overnight for selection of the plasmid. Eight colonies that grew on the plates were picked with sterile toothpicks and grown overnight at 37° C., 250 rpm in a 15 ml FALCON® tube containing 3 ml of LB medium supplemented with 100 μg of ampicillin per ml. The plasmids were isolated using a BioRobot 9600.

Figure 15:
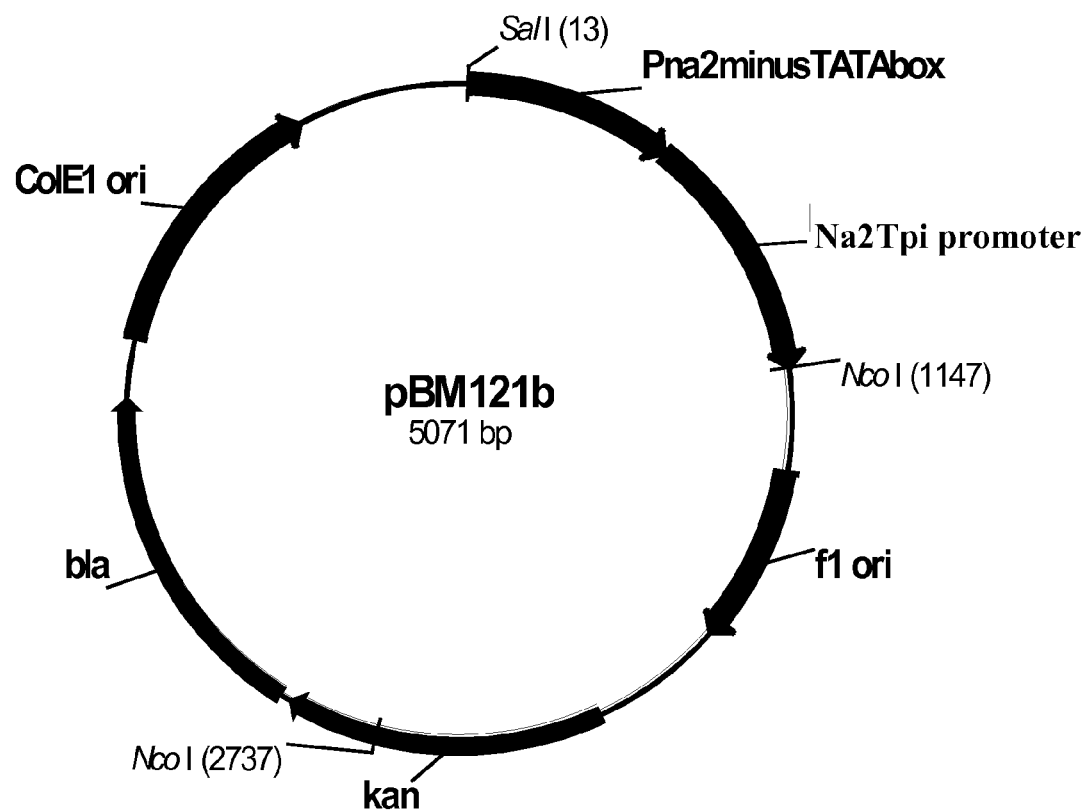
FIG. 15 shows a restriction map of pBM121b.

Four μl volumes of the resulting plasmid minipreps were digested with Eco RI. The digestion reactions were analyzed by agarose gel chromatography and UV analysis as previously described for the PCR reaction. Isolated plasmids containing an insert were sequenced using 1 μl of plasmid template, 1.6 ng of M13 primer (forward or reverse), and water to 6 μl. The resulting plasmid was designated pBM121b (FIG. 15).

Figure 16:
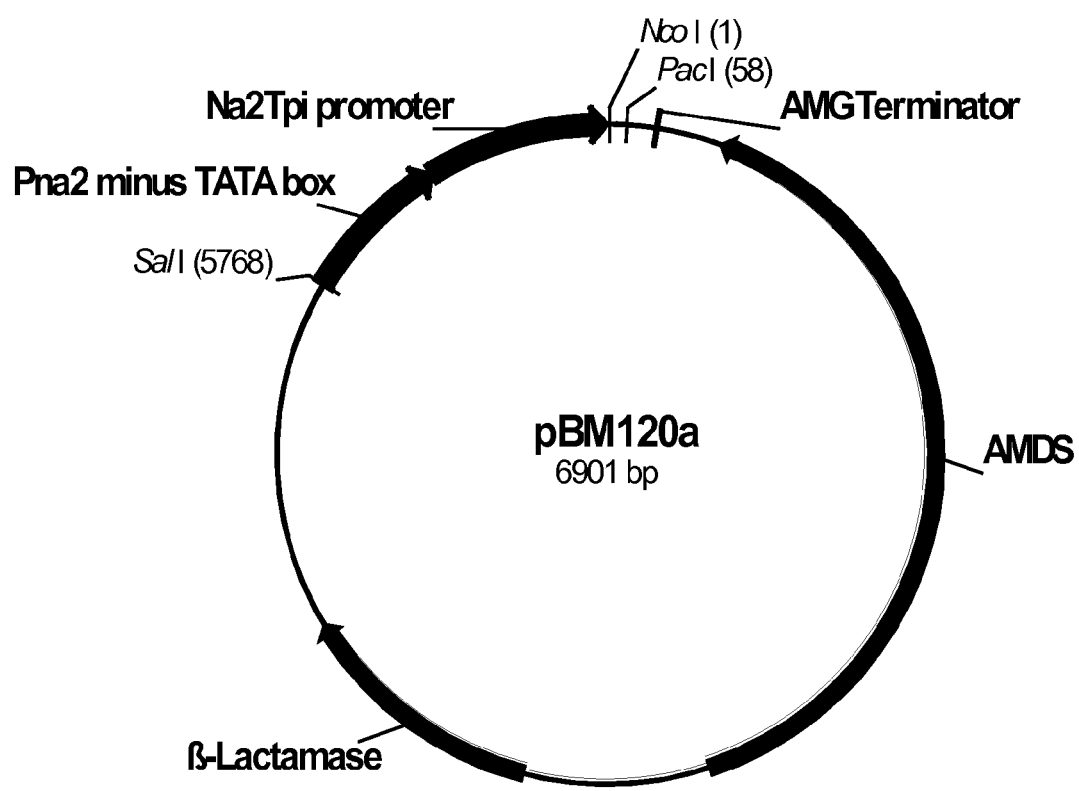
Figure 17:
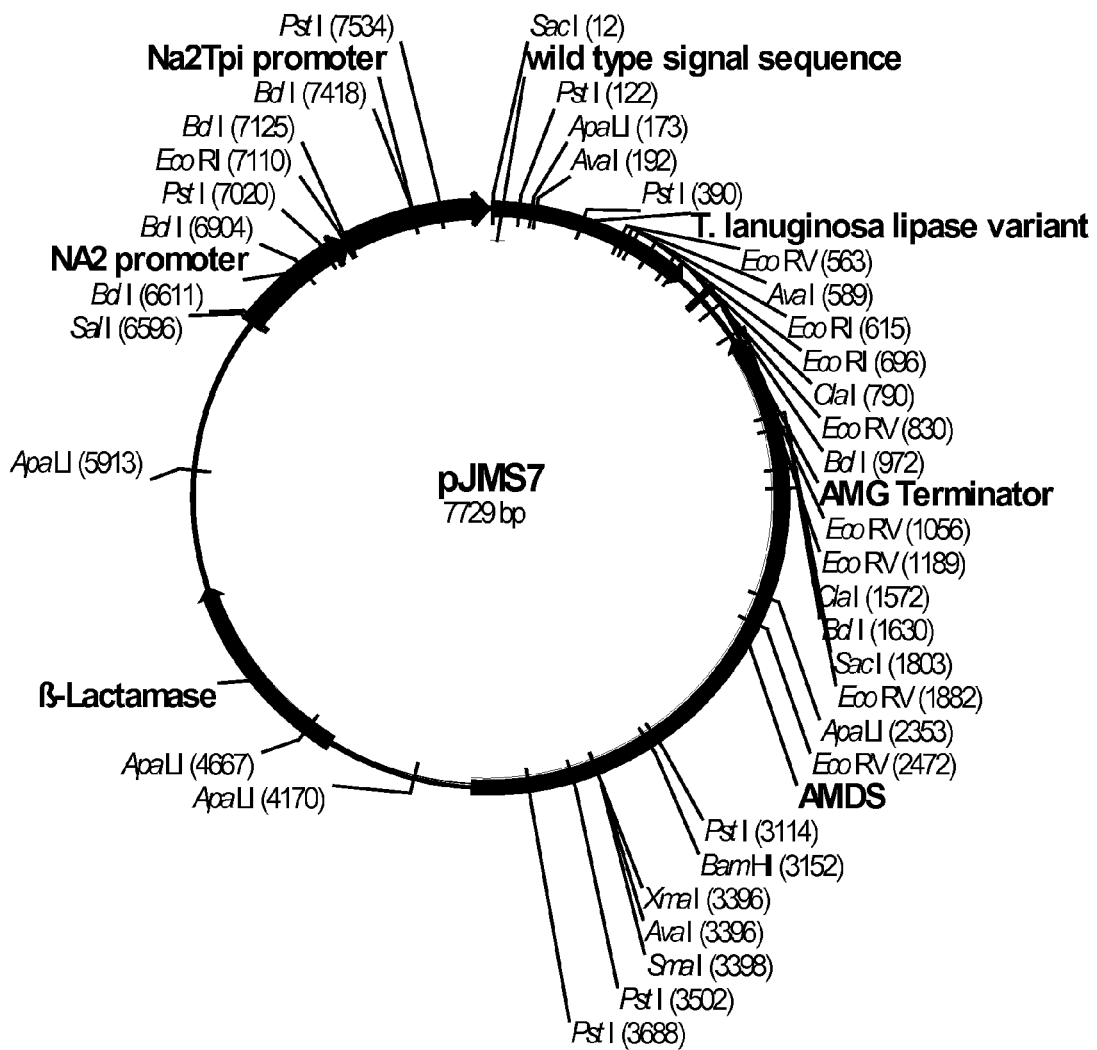
FIG. 17 shows a restriction map of pJMS7.

A 5 μl volume of pBM121b was digested with Sal I and Nco I. The digestion reactions were analyzed by agarose gel electrophoresis as described above, and ligated to the vector pAlLo1, which had been previously digested with Sal I and Nco I. The resulting expression plasmid was designated pBM120a (FIG. 16).

Example 16

Construction of an *Aspergillus oryzae* Vector Containing the *Thermomyces lanuginosa* Lipase Variant Gene The *Thermomyces lanuginosus* lipase variant gene was PCR amplified from pJLin187, an *Aspergillus* expression vector harboring the lipase variant gene. The lipase gene in pJLin187 contained a mutation encoding the amino acid change L269I which was corrected during PCR. The gene was PCR amplified using an EXPAND® High Fidelity PCR System using gene specific primers shown below.

```
Forward primer:
                                      (SEQ ID NO: 27)
5'-ACACAACTGGCCATGAGGAGCTCCCTTGTGCTGTTC-3'

Reverse primer:
                                      (SEQ ID NO: 28)
5'-AGTCACCTCTAGTTAATTAATTATCAAAgACATGTCCCAATTAA
CCC-3'
```

The bold letters represent coding sequence, the underlined portion denotes the introduced Pac I site, the lower case letter is the intended change, and the remaining sequences are flanking regions homologous to the point of insertion in pBM120.

The PCR reaction contained 100 ng of pJLin187, 200 μM dNTP's, 300 nM of each primer, 1× EXPAND® High Fidelity buffer (with MgCl$_2$) and 2.6 units of EXPAND® High Fidelity Enzyme Mix. An EPPENDORF® MASTERCYCLER® was used for the amplification programmed for 1 cycle at 94° C. for 2 minutes; 10 cycles each at 94° C. for 15 seconds, 55° C. for 30 seconds, and 72° C. for 1 minute; and 15 cycles each at 94° C. for 15 seconds, 55° C. for 30 seconds, and 72° C. for 1 minute followed by an additional 5 seconds added to the 72° C. elongation step after each of the 15 cycles.

The PCR reaction mixture was run on a 1% agarose gel using TAE buffer and a band corresponding to the 913 bp insert was excised. The DNA fragment was extracted from the sample by a MINELUTE® Agarose Extraction Kit (QIAGEN Inc., Valencia, Calif., USA) according to the manufacturer's protocol.

An INFUSION® Cloning Kit was used to clone the PCR product directly into expression vector pBM120 without the need for restriction digestion and ligation. The INFUSION® cloning reaction was composed of 1× INFUSION® Reaction Buffer, 1×BSA, 100 ng of pBM120 digested with Pac I and Nco I, 108.4 ng of purified PCR Insert, and 1 μl of INFUSION® enzyme (diluted 1:10). The reaction was incubated at room temperature for 30 minutes and 1 μl was used to transform SOLOPACK® Gold Supercompetent Cells (Stratagene,

Example 17

Construction of an *Aspergillus oryzae* Vector with R2K Signal Peptide and SPIRR Deleted The *Thermomyces lanuginosus* lipase variant gene with the signal peptide sequence change of R2K and SPIRR (SEQ ID NO: 36) deletion was PCR amplified from pJLin195 harboring the gene for the *Thermomyces lanuginosa* lipase variant gene. The gene was PCR amplified using the primers below.

```
Forward primer:
                                        (SEQ ID NO: 29)
5'-CTCTATATACACAACTGGCCATGAAGAGCTCCCTTGTGCTGTTC-3'

Reverse primer:
                                        (SEQ ID NO: 30)
5'-CAGGTGTCAGTCACCTCTAGTTATCAAAGACATGTCCCAATTAA
CCC-3'
```

The bold sequences correspond to *Thermomyces lanuginosa* lipase variant coding regions and the remainder sequences are flanking regions homologous to the point of insertion in pBM120. The PCR reaction and thermocycling conditions were identical to those used for the *Thermomyces lanuginosus* lipase variant gene in Example 16. The PCR reaction was run on an 1% agarose gel using TAE buffer and the DNA fragment was extracted as described in Example 16.

Figure 18:
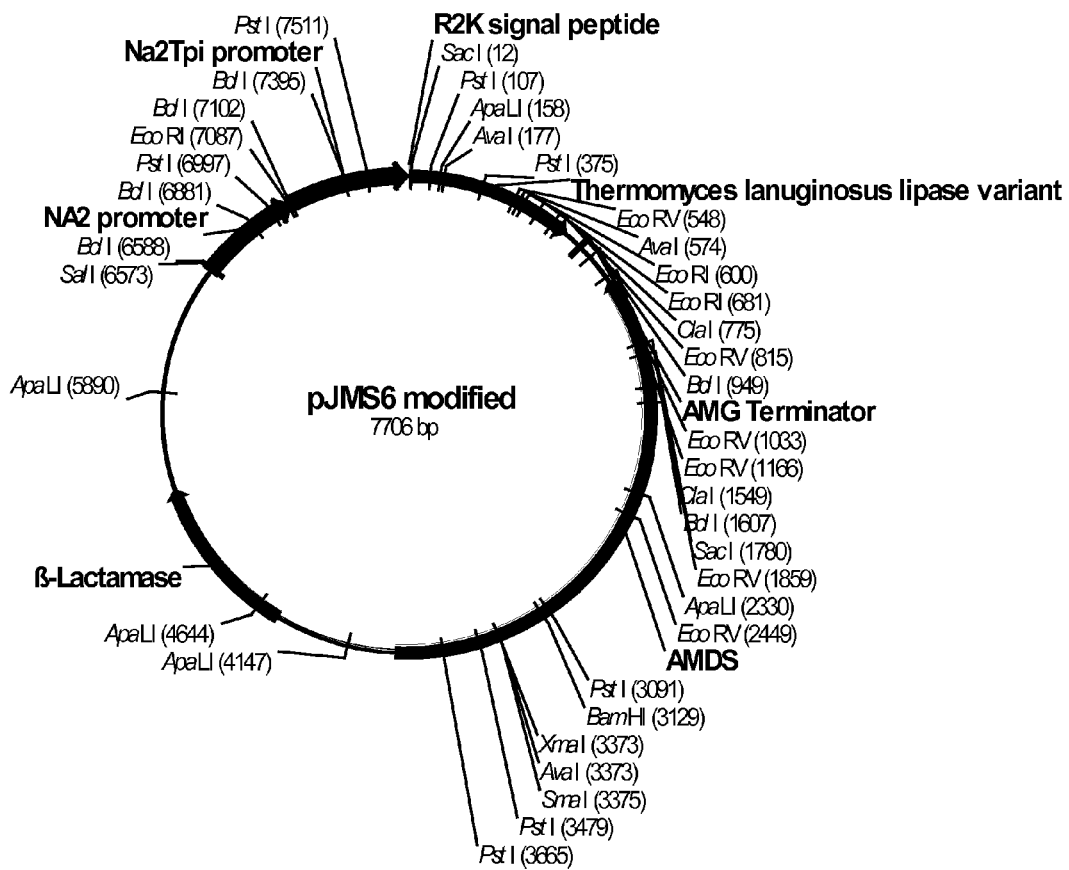
FIG. 18 shows a restriction map of pJMS6.

An NFUSION® Cloning Kit was used to clone the PCR product directly into expression vector pBM120. The INFUSION® reaction was identical to that in Example 16 except 64 ng of the purified PCR insert was used. One µl of the reaction was used to transform SOLOPACK® Gold Supercompetent Cells using the manufacturer's suggested protocols. DNA sequencing confirmed that no errors were introduced by PCR. The resulting plasmid was designated pJMS6 (FIG. 18).

Example 18

Construction of an *Aspergillus oryzae* Vector with R2K Signal Peptide Mutation A QUIKCHANGE® II XL Site-Directed Mutagenesis Kit (Stratagene, La Jolla, Calif., USA) was used to mutate plasmid pJMS7 by changing R to K in the signal peptide sequence of the *Thermomyces lanuginosus* lipase variant gene. The mutagenesis reaction consisted of three steps: mutant strand synthesis using the mutagenic primers shown below, Dpn I digestion of template, and transformation.

```
Forward primer:
                                        (SEQ ID NO: 31)
5'-CACAACTGGCCATGaagAGCTCCCTTGTG-3'

Reverse primer:
                                        SEQ ID NO: 32)
5'-CACAAGGGAGCTcttCATGGCCAGTTGTG-3'
```

The lower case codons indicated the change in the signal sequence.

The mutant strand synthesis reaction was composed of 5 µl of 10× reaction buffer (Stratagene, La Jolla, Calif., USA), 10 ng of pJMS7, 125 ng of each primer, 1 µl of dNTP mix, 3 µl of QUIKSOLUTION® (Stratagene, La Jolla, Calif., USA), and 2.5 units of Pfu Ultra HF DNA polymerase. An EPPENDORF® MASTERCYCLER® was used for the amplification programmed for 1 cycle at 95° C. for 1 minute; 18 cycles each at 95° C. for 50 seconds, 60° C. for 50 seconds, and 68° C. for 7 minutes; and 1 cycle at 68° C. for 7 minutes. One µl of Dpn I restriction enzyme (10 U/µl) was then added to the reaction. After gentle and thorough mixing, the reaction mixture was centrifuged for 1 minute at 13,000×g and immediately incubated at 37° C. for an hour to digest the parental supercoiled dsDNA. Two µl of the Dpn I-treated sample reaction was transformed into 45 µl of *E. coli* XL 10-Gold ultracompetent cells (Stratagene, La Jolla, Calif., USA) following the manufacturer's instructions. After 16 hours, the colonies were picked and submitted for plasmid preparation and sequence analysis. The sequencing primer, shown below, sits in the NA2-tpi promoter region and reads in the forward direction of the *Thermomyces lanuginosus* lipase variant gene.

```
                                        (SEQ ID NO: 33)
5'-ATACTGGCAAGGGATGCCATGCTTGG-3'
```

Correct clones with the R2K mutation in the signal sequence were identified. The resulting plasmid was designated plasmid TB5.

Example 19

Construction of an *Aspergillus oryzae* Vector with SPIRR (SEQ ID NO: 36) Deleted A QUIKCHANGE® II XL Site-Directed Mutagenesis Kit was used to create TB6 from pJMS6 by changing the K to R in the signal sequence region using the mutagenic primers shown below. The mutagenesis procedures were identical to those described in Example 18.

```
Forward primer:
                                        (SEQ ID NO: 34)
5'-CACAACTGGCCATGaggAGCTCCCTTGTG-3'

Reverse primer:
                                        (SEQ ID NO: 35)
5'-CACAAGGGAGCTcctCATGGCCAGTTGTG-3'
```

The lower case codons are the intended change.

Correct clones with SPIRR deletion in the propeptide sequence were identified by DNA sequencing using the primer of SEQ ID NO: 33. The resulting plasmid was designated plasmid TB6.

Example 20

Expression of *Thermomyces lanuginosus* Lipase Variant from pJMS6, pJMS7, Plasmid TB5, and Plasmid TB6

Protoplast preparation and transformation of *Aspergillus oryzae* BeCh2 were performed according to standard protocols, e.g., Christensen et al., 1988, *Bio/Technology* 6: 1419-1422. About 5 µg of each expression vector was used in each transformation reaction. The transformation mixtures were plated onto COVE plates and incubated at 37° C. for 7 days. Transformants were picked and transferred to fresh COVE plates and grown at 34° C. waiting for spore purification and tributyrin assay.

Tributyrin plates were prepared by pouring a 50 ml mixture of 10% (v/v) tributyrin with VNO$_3$RLMT agar (melted and blended in a sterile blender) into 150 mm round plates and allowed to dry. A small 1 cm×1 cm plug of spores was cut out using a sterile toothpick and transferred to a tributyrin plate. Each plate can hold up to 9 μlugs. The plates were incubated for 3-4 days at 34° C. and positive transformants were identified by a halo of clearing around the plugs.

Transformation of *Aspergillus oryzae* Bech2 with pJMS6, pJMS7, plasmid TB5, and plasmid TB6 yielded many transformants that were positive for lipase activity on the tributyrin plates (see table below).

TABLE 1

Number of Transformants Positive for Lipase Activity

| Experiment Number (Example #) | pJMS7 *T. lanuginosus* lipase variant (Example 16) | pJMS6 SPIRR minus and R2K mutation (Example 17) | Plasmid TB5 R2K mutation with SPIRR (Example 18) | Plasmid TB6 SPIRR minus with wild-type signal peptide (Example 19) |
|---|---|---|---|---|
| 1 | 13 | 19 | N/A | N/A |
| 2 | 26 | 32 | N/A | N/A |
| 3 | 17 | 23 | 15 | N/A |
| 4 | 39 | N/A | N/A | 43 |

Positive transformants were streaked onto fresh COVE plates and were grown for 1 to 2 days at 34° C. Two single spores from each streaked plate were picked and transferred to separate COVE plates. These spores were grown at 34° C. for about 7 days. Another tributyrin screening was performed to confirm the lipase activity prior to shake flask analysis.

The spores from positive transformants were collected in approximately 5 ml of 0.01% Tween-20. Two hundred μl of spore suspensions were then used to inoculate 25 ml of MY25 medium in 125 polycarbonate Erlenmeyer flasks. In order to examine the variances between flasks, each spore-purified transformant was inoculated in duplicate. Cultures were incubated for 5 days at 34° C. on a platform shaker at 200 rpm. On day 3, 4, and 5, culture supernatants were collected by centrifugation at 13,000×g for 10 minutes to remove mycelia and stored at −20° C. for automated lipase activity assays.

To determine lipase activity in the culture supernatants an automated assay using a BIOMEK® 3000 (Beckman Coulter, Inc, Fullerton, Calif., USA) was used. Culture supernatants were diluted appropriately (1/10, 1/50, and/or 1/100) in 0.1 M MOPS, 4 mM CaCl$_2$, 0.01% Triton X-100 buffer pH 7.5 (sample buffer) (to prevent proteins sticking to the plate) followed with a series dilution from 0-fold to 1/3-fold to 1/9-fold of the diluted sample. A LIPOLASE™ standard (Novozymes NS, Bagsværd, Denmark) was diluted using 2-fold steps starting with a 1.0 LU/ml concentration and ending with a 0.125 LU/ml concentration in the sample buffer. A total of 20 μl of each dilution including standard was transferred to a 96-well flat bottom plate. Two hundred microliters of a p-nitrophenyl butyrate substrate solution (ratio of p-nitrophenyl butyrate to DMSO to 0.1 M MOPS pH 7.5 was 1:99:400) was added to each well and then incubated at ambient temperature for 6.5 minutes. During the incubation the rate of the reaction was measured at 405 nm. Sample concentrations were determined by extrapolation from the generated standard curve.

Figure 19:
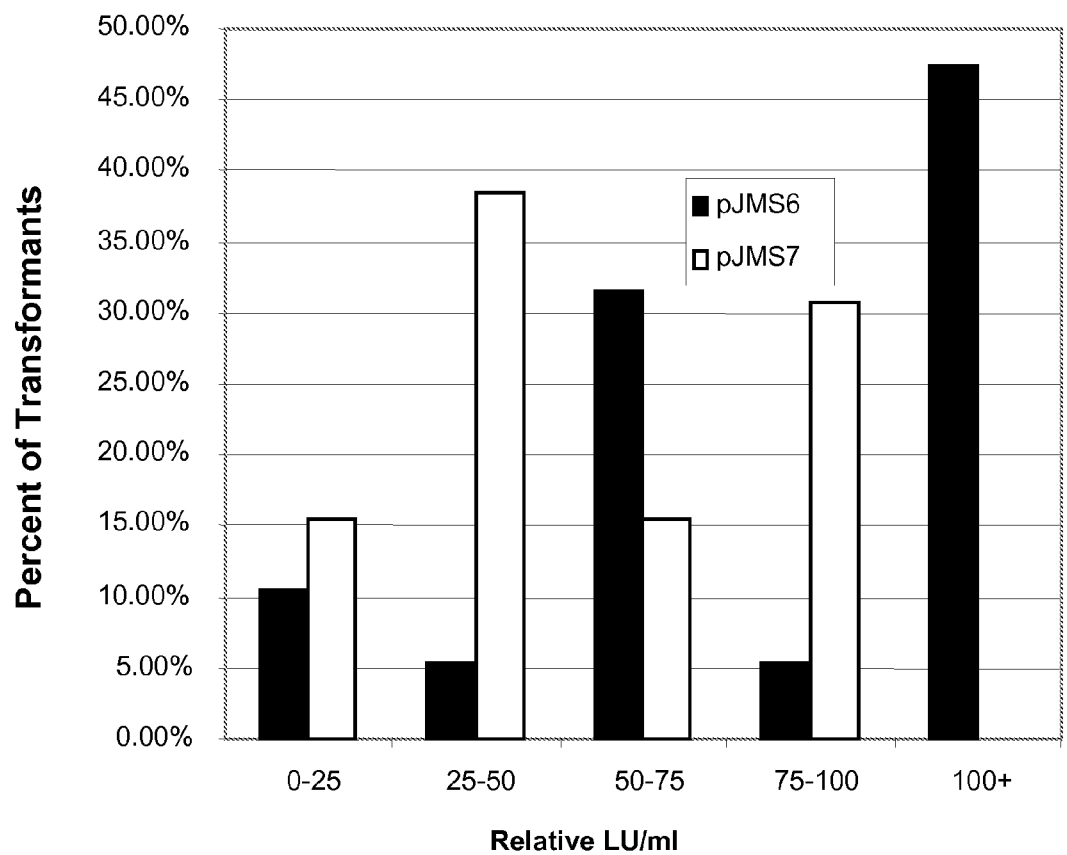
FIG. 19 shows the relative lipase activities for day 3 culture broths of transformants of pJMS6 and pJMS7.

Comparison of the yields (relative LU/ml) obtained from transformants containing pJMS7 (*Thermomyces lanuginosus* lipase variant) and pJMS6 (SPIRR (SEQ ID NO: 36) minus with R2K change) are shown in FIG. 19.

The results showed that deletion of SPIRR (SEQ ID NO: 36) in combination with the R2K change improved expression compared to the wild-type gene. A t-test of the two populations yielded a p value of less than 0.007.

Figure 20:
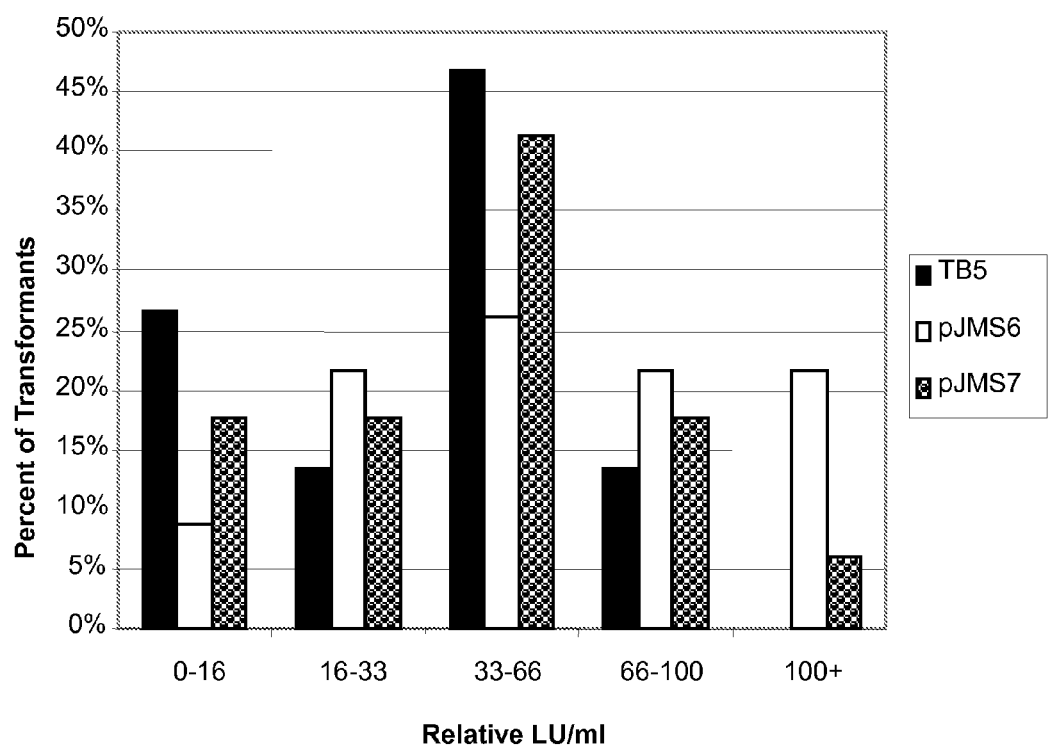
FIG. 20 shows the relative lipase activities for day 3 culture broths of transformants of pJMS6, pJMS7, and plasmid TB5.

Comparison of the yields (relative LU/ml) obtained from transformants containing pJMS7 (*Thermomyces lanuginosus* lipase variant), pJMS6 (SPIRR (SEQ ID NO: 36) minus with R2K change), and plasmid TB5 (R2K change) are shown in FIG. 20. The results showed that the R2K change alone does not result in increased yields relative to the wild-type gene and in fact may lead to a slight decrease. A t-test of the comparing the pJMS7 and plasmid TB5 populations yielded a p value of 0.047.

Figure 21:
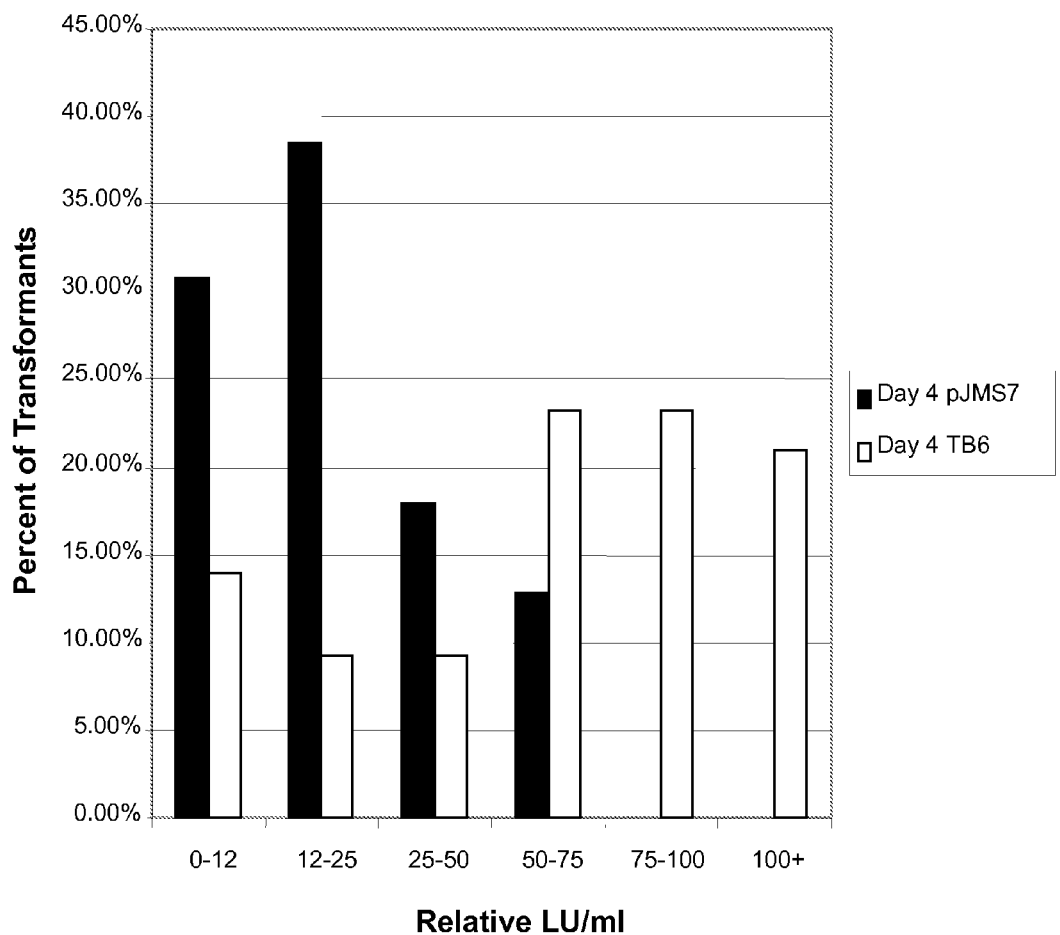
FIG. 21 shows the relative lipase activities for day 4 culture broths of transformants of pJMS6 and plasmid TB6.

Comparison of the yields (relative LU/ml) obtained from transformants containing pJMS7 (*Thermomyces lanuginosus* lipase variant) and plasmid TB6 (SPIRR (SEQ ID NO: 36) minus) are shown in FIG. 21.

The results showed that the SPIRR (SEQ ID NO: 36) deletion alone gives an increased yield relative to the wild-type gene. A t-test of the comparing the pJMS7 and plasmid TB6 populations yielded a p value of less than $7.7 \times 10^{-7}$.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An genetically engineered and isolated polynucleotide, which encodes a signal peptide variant consisting of amino acids 1 to 17 of SEQ ID NO: 2 without amino acids "SPIRR" wherein the amino acid residue 2 is substituted with Lys, and wherein the encoded signal peptide is directly fused in frame to the amino terminus of a mature polypeptide of interest which is encoded by said polynucleotide.

2. A nucleic acid construct comprising the polynucleotide of claim 1.

3. The nucleic acid construct of claim 2, wherein the polynucleotide encoding the signal peptide variant is operably linked to a second polynucleotide encoding a polypeptide, wherein the 3' end of the signal peptide polynucleotide is immediately upstream of the start codon of the second polynucleotide.

4. A recombinant expression vector comprising the nucleic acid construct of claim 3.

5. A recombinant host cell transformed with the nucleic acid construct of claim 3.

6. The recombinant host cell of claim 5, wherein the host cell is a yeast host cell.

7. The recombinant host cell of claim 5, wherein the host cell is a filamentous fungal host cell.

8. The recombinant host cell of claim 5, wherein the host cell is an *Aspergillus* host cell.

9. The recombinant host cell of claim 8, wherein the *Aspergillus* host cell is an *Aspergillus oryzae* host cell.

10. The recombinant host cell of claim 5, wherein the host cell is a *Saccharomyces* host cell.

11. The recombinant host cell of claim 10, wherein the *Saccharomyces* host cell is a *Saccharomyces cerevisiae* host cell.

12. The recombinant host cell of claim 5, wherein the host cell produces at least 25% more mature polypeptide relative to an otherwise identical host cell that expresses the sequence of SEQ ID NO: 2 which does not comprise said substitution and is directly fused in frame to the amino terminus of the encoded mature polypeptide.

13. The polynucleotide of claim 1, wherein the signal peptide variant consists of SEQ ID NO: 4.

14. The polynucleotide of claim 1, wherein the nucleotide sequence encoding the mature polypeptide encodes a heterologous polypeptide.

15. The polynucleotide of claim 1, wherein the nucleotide sequence encoding the mature polypeptide encodes a lipase.

* * * * *